(12) United States Patent
Michel et al.

(10) Patent No.: US 11,154,625 B2
(45) Date of Patent: Oct. 26, 2021

(54) FUCOIDANS AS LIGANDS FOR THE DIAGNOSIS OF DEGENERATIVE PATHOLOGIES

(71) Applicant: INSERM (Institut National de la Sante et de la Recherche Medicale), Paris (FR)

(72) Inventors: Jean-Baptiste Michel, Paris (FR); Didier Letourneur, Paris (FR); Frederic Chaubet, Paris (FR); Laure Bachelet, Paris (FR); Francois Rouzet, Paris (FR); Alain Meulemans, Paris (FR)

(73) Assignees: INSERM (INSTITUT NATIONAL DE LA SANTE ET DE LA RECHERCHE MEDICALE), Paris (FR); UNIVERSITE PARIS 13, Paris (FR)

( * ) Notice: Subject to any disclaimer, the term of this patent is extended or adjusted under 35 U.S.C. 154(b) by 361 days.

(21) Appl. No.: 14/158,235

(22) Filed: Jan. 17, 2014

(65) Prior Publication Data
US 2014/0134102 A1 May 15, 2014

Related U.S. Application Data

(60) Division of application No. 13/346,075, filed on Jan. 9, 2012, now abandoned, which is a continuation-in-part of application No. 13/259,802, filed as application No. PCT/IB2009/052791 on Apr. 10, 2009, now abandoned.

(51) Int. Cl.

| | |
|---|---|
| A61K 51/06 | (2006.01) |
| G01N 33/53 | (2006.01) |
| A61K 49/22 | (2006.01) |
| A61K 49/18 | (2006.01) |
| A61K 49/04 | (2006.01) |
| G01N 33/68 | (2006.01) |
| G01N 33/574 | (2006.01) |
| C08B 37/00 | (2006.01) |
| C08L 5/00 | (2006.01) |
| A61K 49/06 | (2006.01) |
| A61K 51/00 | (2006.01) |

(52) U.S. Cl.
CPC ........... *A61K 51/065* (2013.01); *A61K 49/04* (2013.01); *A61K 49/0438* (2013.01); *A61K 49/06* (2013.01); *A61K 49/1863* (2013.01); *A61K 49/22* (2013.01); *A61K 49/221* (2013.01); *A61K 49/223* (2013.01); *A61K 51/00* (2013.01); *C08B 37/0063* (2013.01); *C08L 5/00* (2013.01); *G01N 33/53* (2013.01); *G01N 33/574* (2013.01); *G01N 33/6893* (2013.01); *G01N 33/6896* (2013.01); *G01N 2333/405* (2013.01); *G01N 2333/4724* (2013.01); *G01N 2400/00* (2013.01); *G01N 2800/102* (2013.01); *G01N 2800/28* (2013.01); *G01N 2800/32* (2013.01)

(58) Field of Classification Search
None
See application file for complete search history.

(56) References Cited

U.S. PATENT DOCUMENTS 4,385,046 A    5/1983   Milbrath et al.
5,962,424 A *  10/1999  Hallahan ............... A61K 41/00
                                                424/455

FOREIGN PATENT DOCUMENTS

WO    WO 2006012201 A1 *  2/2006  ........... A61K 49/183

OTHER PUBLICATIONS

Hallek et al. Guidelines for the diagnosis and treatment of chronic lymphocytic leukemia: a report from the International Workshop on Chronic Lymphocytic Leukemia updating the National Cancer Institute-Working Group 1996 guidelines. 2008 Blood 111: 5446-5456. Published online Jan. 23, 2008.*
Varki A. Selectin ligands. 1994 Proc. Natl. Acad. Sci. USA 91: 7390-7397.*
Griffiths et al. Radiolabeling of monoclonal antibodies and fragments with technetium and rhenium. 1992 Bioconjug. Chem. 3: 91-99.*
Laforest et al. Pharmacokinetics and biodistribution of technetium 99m labelled standard heparin and a low molecular weight heparin (enoxaparin) after intravenous injection in normal volunteers. 1991 Br. J. Haematol. 77: 201-208.*
Fritzsche et al. The influence of various structural parameters of semisynthetic sulfated polysaccharides on the P- selectin inhibitory capacity. 2006 Biochem. Pharmacol. 72: 474-485.*
Gruber et al. Monoclonal antibodies in cancer therapy. 1996 Springer Semin. Immunopathol. 18: 243-251.*
Machac et al. Peptide and antibody imaging in lung cancer. 2002 Semin. Nucl. Med. 32: 276-292. (Year: 2002).*
Xu et al. A potential thrombus diagnosis reagent based on P-selectin monoclonal antibody SZ-51 light chain. 2008 Thromb. Res. 123: 306-315. Epub Aug. 9, 2008. (Year: 2008).*

(Continued)

*Primary Examiner* — Jennifer Lamberski
(74) *Attorney, Agent, or Firm* — W&C IP

(57) ABSTRACT

The present invention relates to the diagnosis of clinical conditions characterized by undesirable and/or abnormal selectin expression. In particular, the invention provides for the use of fucoidans for the detection of selectins using imaging techniques including ultrasonography, scintigraphy and MRI. Selectin-targeted imaging agents are provided that comprise at least one fucoidan moiety associated with at least one detectable moiety. Methods and kits are described for using these imaging agents in the diagnosis of clinical conditions such as thrombosis, myocardial ischemia/reperfusion injury, stroke and ischemic brain trauma, neurodegenerative disorders, tumor metastasis and tumor growth, and rheumatoid arthritis.

4 Claims, 11 Drawing Sheets

(56) References Cited

OTHER PUBLICATIONS

Blankenberg et al. 99mTc-HYNIC-annexin V SPECT imaging of acute stroke and its response to neuroprotective therapy with anti-Fas ligand antibody. 2006 Eur. J. Nucl. Med. Mol. Imaging 33: 566-574. (Year: 2006).*
Connolly et al. Exacerbation of cerebral injury in mice that express the P-selectin gene: identification of P-selectin blockade as a new target for the treatment of stroke. 1997 Circ. Res. 81: 304-310. (Year: 1997).*
Sun et al. Resveratrol as a therapeutic agent for neurodegenerative diseases. 2010 Mol. Neurobiol. 41: 375-383. Epub Mar. 21, 2010. (Year: 2010).*
Mehta et al. Excitotoxicity: bridge to various triggers in neurodegenerative disorders. 2013 Eur. J. Pharmacol. 698: 6-18. Epub Oct. 30, 2012. (Year: 2012).*
Kulkarni et al. Technetium-labeled heparin: preliminary report of a new radiopharmaceutical with potential for imaging damaged coronary arteries and myocardium. 1978 J. Nucl. Med. 19.7:810-815. (Year: 1978).*
Palazzo et al. Coronary endothelial P-selectin in pathogenesis of myocardial ischemia-reperfusion injury. 1998 Am. J. Physiol. 275: H1865-H1872. (Year: 1998).*
Bachelet et al., "Affinity of low molecular weight fucoidan for P-selectin triggers its binding to activated human platelets," Biochim. Biophys. Acta, 1790(2):141-146 (2009) XP025868654.
Giraux et al., "Modulation of human endothelial cell proliferation and migration by fucoidan and heparin," Eur. J. Cell Biol., 77:352-359 (1998).
Gratz et al., "(99m)Tc-E-selectin binding peptide for imaging acute osteomyelitis in a novel rat model," Nucl. Med. Commun., 22(9):1003-1013 (2001) XP009076103.
Hariri et al., "Radiation-guided P-selection antibody targeted to lung cancer," Ann. Biomed. Eng., 36(5):821-830 (2008) XP019598332.
International Search Report in PCT/IB2009/052791, dated Jan. 27, 2010.
Li et al., "Fucoidan: structure and bioactivity," Molecules, 13:1671-1695 (2008).
Pedron et al., "Down-modulation of L-selectin by lipopolysaccharide is not required for lipopolysaccharide-induced expression of CD14 in mouse bone marrow granulocytes," Infect. Immun., 69:4287-4294 (2001).
Vass et al., "Biotinylated L-selectin ligand analogs as cytochemical probes in cytospin preparations," Folia Histochem. Cytobiol., 33(1):39-41 (1995) XP008114481.
Yoshida et al., "A liquid-phase binding analysis of L-selectin. A strong dependency on highly clustered sulfate groups," Eur. J. Biochem., 222(2):703-709 (1994) XP000614583.
Dilworth, Jonathan R. et al, "The biomedical chemistry of technetium and rhenium" Chemical Society Reviews, 1998, vol. 27, pp. 43-55.
Johannsen, Bernd et al, "Development of technetium-99m-based CNS receptor ligands: have there been any advances?" European Journal of Nuclear Medicine, vol. 29, No. 2, Feb. 2002.
Braband, Henrik "High-valent technetium chemistry—new opportunities for radiopharmaceutical developments" Journal of Labelled Compounds and Radiopharmaceuticals, 2014, vol. 57, pp. 270-274.
Strauss et al, "Procedure Guideline for Myocardial Perfusion Imaging 3.3" Myocardial Perfusion Imaging, Journal of Nuclear Medicine Technology, vol. 36, No. 3, Sep. 2008, pp. 155-161.
Sogbein et al, "New SPECT and PET Radiopharmaceuticals for Imaging Cardiovascular Disease" BioMed Research International, May 11, 2014.

* cited by examiner

FUCOIDANS AS LIGANDS FOR THE DIAGNOSIS OF DEGENERATIVE PATHOLOGIES

RELATED APPLICATION

The present patent application is a divisional application of U.S. patent application Ser. No. 13/346,075, filed Jan. 9, 2012, which is a continuation-in-part of patent application Ser. No. 13/259,802, which was itself filed pursuant to 35 U.S.C. § 371 as a U.S. National Phase application of International Patent Application No. PCT/162009/052791, filed Apr. 10, 2009. The entire content of the above applications is incorporated herein by reference in its entirety.

BACKGROUND OF THE INVENTION

Numerous human degenerative diseases, including cardiovascular degenerative diseases, but also organ-specific degenerative diseases, involve circulating cell/vascular wall interactions. Selectins are important cell adhesion molecules, with high affinities for carbohydrate moieties. They play a prominent and critical role in the initial stages of circulating cellular components and vascular wall interactions by mediating leucocytes/platelet and leucocytes/endothelium interactions. Three types of selectins have been discovered so far: P-selectin, E-selectin and L-selectin. L-selectin is constitutively expressed on almost all circulating leukocytes. The expression of E-selectin is inducible on vascular endothelium upon activation by various mediators including cytokines and endotoxin. P-selectin is contained in intracytoplasmic granules and is rapidly translocated to platelet or endothelial surfaces after cell exposure to thrombin or histamine.

The P-, L- and E-selectins are structurally similar transmembrane proteins. They all possess large, highly glycosylated, extracellular domains, a single spanning transmembrane domain, and a small cytoplasmic tail. At their extracellular amino termini, they have a single calcium-dependent (or C-type) lectin domain (L) followed by an epidermal growth factor (EGF)-like domain (E) and several complement regulatory domains (C). Selectin-mediated cell adhesion results from calcium-dependent interactions of the amino-terminal lectin domain with a large variety of carbohydrate-presenting molecules on the surface of target cells. While the affinity of each of the selectins varies depending on the ligand, they all bind a specific tetrasaccharide carbohydrate structure known as sialyl Lewis X (SLe$^X$), which contains sialic acid and fucose residues.

Although selectin-mediated binding events play a critical role in normal physiological processes, selectins are also known to contribute to many pathologies. Such pathologies include clinical conditions that are associated with platelet activation and fibrin formation such as atherothrombotic diseases (E. Galkina et al., Curr. Drug Targets, 2007, 8: 1239-1248); clinical conditions associated with acute endothelial activation such as sepsis, brain ischemia, or ischemia-reperfusion (C. R. Calvey et al., J. Invest. Surg., 2007, 20: 71-85); clinical conditions associated with chronic endothelial activation such as hypertension, hyperlipidemia, obesity (S. Nishimura et al., J. Clin. Invest., 2008, 118: 710-721) and degenerative disorders of the cardiovascular system, the lung or the brain (M. Fisher, Rev. Neurol. Dis., 2008, 5 Suppl. 1: S4-S11; S. I. van Kasteren et al., Proc. Natl. Acad. Sci. USA, 2009, 106: 18-23); and clinical conditions associated with chronic focalized accumulation of leukocytes such as tertiary lymphoid neogenesis or autoimmune diseases. Selectin interactions can also mediate adhesive mechanisms involved in the metastasis of certain epithelial cancers (I. P Witz, Immunol. Lett., 2006, 104: 89-93; 1; S. Gout et al., Clin. Exp. Metastasis, 2008, 25: 335-344; L. Borsig, Expert Rev. Anticancer Ther., 2008, 8: 1247-1255).

Selectins are considered as potentially useful markers for the diagnosis of some of these pathologies. Numerous efforts are in progress to image selectins predominantly through Magnetic Resonance Imaging (MRI) (S. Bouty et al., Contrast Media Mol. Imaging, 2006, 1: 15-22), scintigraphy (G. Hairi et al., Ann. Biomed. Eng., 2008, 36: 821-830), and more recently using ultrasons (F. S. Villanueva et al., Nat. Clin. Pract. Cardiovasc. Med., 2008, 5: S26-S32). Most selectin imaging agents developed so far are anti-selectin antibodies (B. A. Kaufman et al., Eur. Heart J., 2007, 28: 2011-2017; G. Hairi et al., Ann. Biomed. Eng., 2008, 36: 821-830; K. Licha et al., J. Biomed. Opt., 2005, 10: 41205; and P. Hauff et al., Radiology, 2004, 231: 667-673) and sialyl Lewis X analogs or derivatives (S. Bouty et al., Contrast Media Mol. Imaging, 2006, 1: 15-22; F. S. Villanueva et al., Circulation, 2007, 115: 345-352). These imaging agents have been demonstrated to allow the in vivo non-invasive detection of selectins in inflammation, neurodegenerative disorders, cancer and thrombosis. However, they exhibit several disadvantages that will certainly preclude their industrial development and commercialization. Indeed, the preparation and purification of sialyl Lewis X-based imaging agents and of antibody-based imaging agents is complex and very costly.

Therefore, there remains a need in the art for new approaches for the imaging and detection of circulating cell/vascular wall interactions allowing the non-invasive diagnosis and/or the preventive screening of diseases such as cardio/neurovascular pathologies, neurodegenerative disorders and cancer metastasis. Selectin imaging agents that are easy and relatively cheap to produce are particularly desirable.

SUMMARY OF THE INVENTION

The present invention relates to improved systems and strategies for the detection of selectins and the diagnosis of diseases and disorders characterized by undesirable or abnormal interactions mediated by selectins. In particular, the invention encompasses the recognition by the Applicants that fucoidans exhibit high affinity, specificity and/or selectivity for selectins. More specifically, the present Applicants have compared the interactions of P-selectin with several low molecular weight (LMW) polysaccharides: fucoidan, heparin and dextran sulfate. Using binding assay, mass spectrometry, surface plasmon resonance and flow cytometry on human platelets, they found that LMW fucoidan is the most efficient ligand of P-selectin (see Example 1). However, a less specific binding of fucoidan to fibrin moieties through hydrogen bonds is not excluded (K. H. Hsieh, Biochemistry, 1997, 36: 9381-9387). The Applicants also showed that LMW fucoidan radiolabelled with Technetium-99m ($^{99m}$Tc) allowed the in vivo detection of endocarditic vegetations, aneurismal and atrial thrombi in animal models (conditions associated with platelet-selectin exposition and fibrin formation) (see Example 2). The Applicants have also developed an MRI contrast agent comprising fucoidan conjugated to USPIOs (ultra small superparamagnetic iron-oxide nanoparticles) which, in a rat model of vascular injury, was found to allow visualization of platelet-rich thrombus with high sensitivity and excellent sensitivity, very soon after injection of the contrast agent and requiring only a short image acquisition time (Example 6).

Accordingly, the present invention provides for the use of fucoidans for the detection and imaging of selectins and for the diagnosis of diseases and disorders characterized by undesirable or abnormal expression of selectins.

More specifically, in one aspect, the present invention provides an imaging agent comprising at least one fucoidan moiety associated with at least one detectable moiety. Preferably, the imaging agent is selectin-targeted. More preferably, the at least one fucoidan moiety of the imaging agent binds to at least one human selectin selected from the group consisting of P-selectin, L-selectin, and E-selectin with a dissociation constant of between about 0.1 nM and about 500 nM, preferably between about 0.5 nM and about 10 nM, more preferably between about 1 nM and about 5 nM.

In certain embodiments, the detectable moiety comprises a metal-chelating moiety complexed to a detectable moiety.

In certain embodiments, the detectable moiety is detectable by planar scintigraphy (PS) or Single Photon Emission Computed Tomography (SPECT). For example, the detectable moiety is a radionuclide selected from the group consisting of technetium-99m ($^{99m}$Tc), gallium-67 ($^{67}$Ga), yttrium-91 ($^{91}$Y), indium-111 ($^{111}$In), rhenium-186 ($^{186}$Re), and thallium-201 ($^{201}$Tl). In certain preferred embodiments, the detectable moiety is technetium-99m ($^{99m}$Tc).

In other embodiments, the detectable moiety is detectable by Positron Emission Tomography (PET). For example, the detectable moiety may be selected from the group consisting of carbon-11 ($^{11}$C), nitrogen-13 ($^{13}$N), oxygen-15 ($^{15}$O) and fluorine-18 ($^{18}$F).

In other embodiments, the detectable moiety is detectable by contrast-enhanced ultrasonography (CEUS). For example, the detectable moiety may be selected from the group consisting of acoustically active microbubbles and acoustically active liposomes.

In still other embodiments, the detectable moiety is detectable by Magnetic Resonance Imaging (MRI). For example, the detectable moiety may be selected from the group consisting of gadolinium III ($Gd^{3+}$), chromium III ($Cr^{3+}$), dysprosium III ($Dy^{3+}$), iron III ($Fe^{3+}$), europium ($Eu^{3+}$), manganese II ($Mn^{2+}$), and ytterbium III ($Yb^{3+}$). In certain preferred embodiments, the detectable moiety is gadolinium III ($Gd^{3+}$). Alternatively, the detectable moiety detectable by MRI may be an ultrasmall superparamagnetic iron oxide particle (USPIO).

In yet other embodiments, the detectable moiety is detectable by fluorescence spectroscopy. For example, the detectable moiety may be selected from the group consisting of europium ($Eu^{3+}$), quantum dots, Texas red, fluorescein isothiocyanate (FITC), phycoerythrin (PE), rhodamine, carboxycyanine, Cy-3, Cy-5, Cy5.5, Cy7, DY-630, DY-635, DY-680, Atto 565 dyes, merocyanine, styryl dye, oxonol dye, BODIPY dyes, and analogues, derivatives or combinations of these molecules. In particular, in certain embodiments, the detectable moiety is detectable by time-resolved fluorometry. For example, the detectable moiety may be europium ($Eu^{3+}$).

In certain embodiments of the present invention, an imaging agent is detectable by more than one imaging technique and may therefore be used in multimodal imaging. For example, an imaging agent may be detectable by any suitable combination of imaging techniques selected from the group consisting of ultrasonography, Magnetic Resonance Imaging (MRI), Positron Emission Tomography (PET), Single Photon Emission Computed Tomography (SPECT), fluorescence spectroscopy, Computed Tomography, and X-ray radiography. In certain embodiments, such an imaging agent comprises at least one fucoidan moiety associated with at least one detectable moiety that is detectable by more than one imaging technique. In other embodiments, such an imaging agent comprises at least one fucoidan moiety associated with a first detectable moiety and a second detectable moiety, wherein the first detectable moiety is detectable by a first imaging technique and the second detectable moiety is detectable by a second imaging technique and the first and second imaging techniques are different.

In certain embodiments, the fucoidan moiety has an average molecular weight of about 2000 to about 8000 Da. In other embodiments, the fucoidan moiety has an average molecular weight of about 20,000 to about 70,000 Da. In yet other embodiments, the fucoidan moiety has an average molecular weight of about 100,000 to about 500,000 Da.

In another aspect, the present invention provides a pharmaceutical composition comprising an effective amount of at least one imaging agent of the invention, or a physiologically tolerable salt thereof, and at least one pharmaceutically acceptable carrier.

In a related aspect, the present invention provides for the use of an imaging agent according to the invention for the manufacture of a composition for the detection and/or imaging of selectins. The present invention also provides for the use of an inventive imaging agent for the manufacture of a composition for the diagnosis of a clinical condition associated with selectins.

In still another aspect, the present invention provides a method for diagnosing a clinical condition associated with selectins in a patient, said method comprising steps of: administering to the patient an effective amount of an imaging agent, or a pharmaceutical composition thereof, according to the invention; and detecting any selectin bound to the imaging agent using an imaging technique.

In a related aspect, the present invention provides an imaging agent disclosed herein for use in an in vivo method of diagnostic of clinical conditions associated with selectins.

Examples of clinical conditions that can be diagnosed using an imaging agent and/or a method of the invention according to the invention are members of the group consisting of thrombosis, myocardial ischemia/reperfusion injury, stroke and ischemic brain trauma, neurodegenerative disorders, tumor metastasis, tumor growth, and rheumatoid arthritis.

In yet another aspect, the present invention provides a method for detecting the presence of abnormal selectins in a biological system, the method comprising steps of: contacting the biological system with an effective amount of an imaging agent, or a pharmaceutical composition thereof, according to the invention; and detecting any selectin bound to the imaging agent using an imaging technique. The biological sample may be a cell, a biological fluid or a biological tissue.

In a related aspect, the present invention provides an imaging agent disclosed herein for use in an in vitro method of diagnostic of clinical conditions associated with selectins.

In certain embodiments, the biological sample originates from a patient suspected of having a clinical condition associated with selectins, and the method is used to diagnose the clinical condition.

In other embodiments, the biological sample originates from a patient who has received a treatment for a clinical condition associated with selectins, and the method is used to monitor the response of a patient to the treatment.

In yet another aspect, the present invention provides kits for the diagnosis of a clinical condition associated with selectins in a patient or for the detection of abnormal selectins in a biological tissue, the kit comprising a selectin-targeted imaging agent according to the invention or comprising a fucoidan moiety, a detectable moiety, and instructions for preparing a selectin-targeted imaging agent described herein using the fucoidan moiety and detectable moiety.

In certain embodiments, the detectable moiety is a short-lived radionuclide selected from the group consisting of technetium-99m ($^{99m}$Tc), gallium-67 ($^{67}$Ga), yttrium-91 ($^{91}$Y), indium-111 ($^{111}$In), rhenium-186 ($^{186}$Re), and thallium-201 ($^{201}$Tl).

The kit may further comprise instructions for diagnosing the clinical condition using the selectin-targeted imaging agent.

These and other objects, advantages and features of the present invention will become apparent to those of ordinary skill in the art having read the following detailed description of the preferred embodiments.

Fifteen minutes after, USPIO-FUCO showed statistically significant attenuation compared to the baseline (*p<0.05, **p<0.001).

Figure 11:
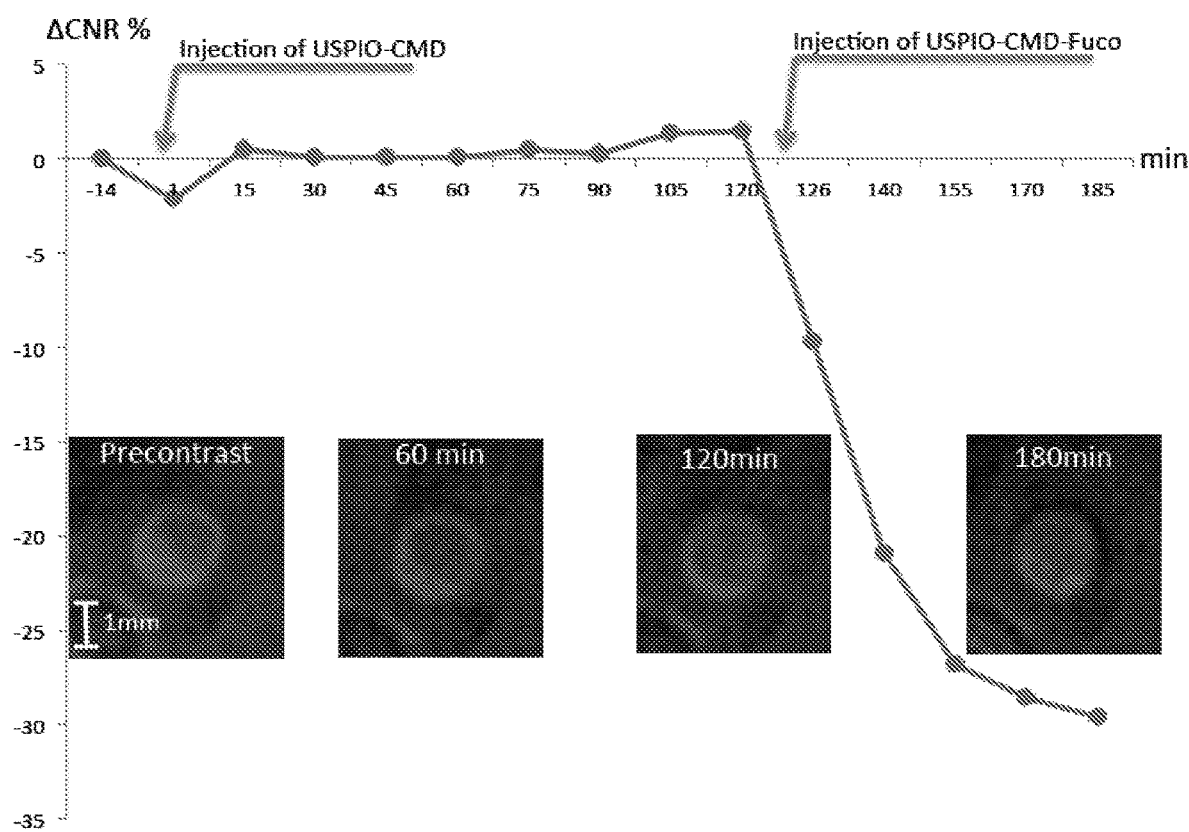

FIG. 11 shows the time table of the variation of the Contrast to Noise Ratio (CNR) before (0-120 minutes) and after (120-185 minutes) injection of USPIO-FUCO. During the first period (0-120 min), the injection of USPIO-CMD (CarboxyMethyl Dextran=control) did not modify the CNR. In contrast, during the second period (120-185 min), the injection of USPIO-FUCO significantly negativates the RMN signal.

Figure 12A:
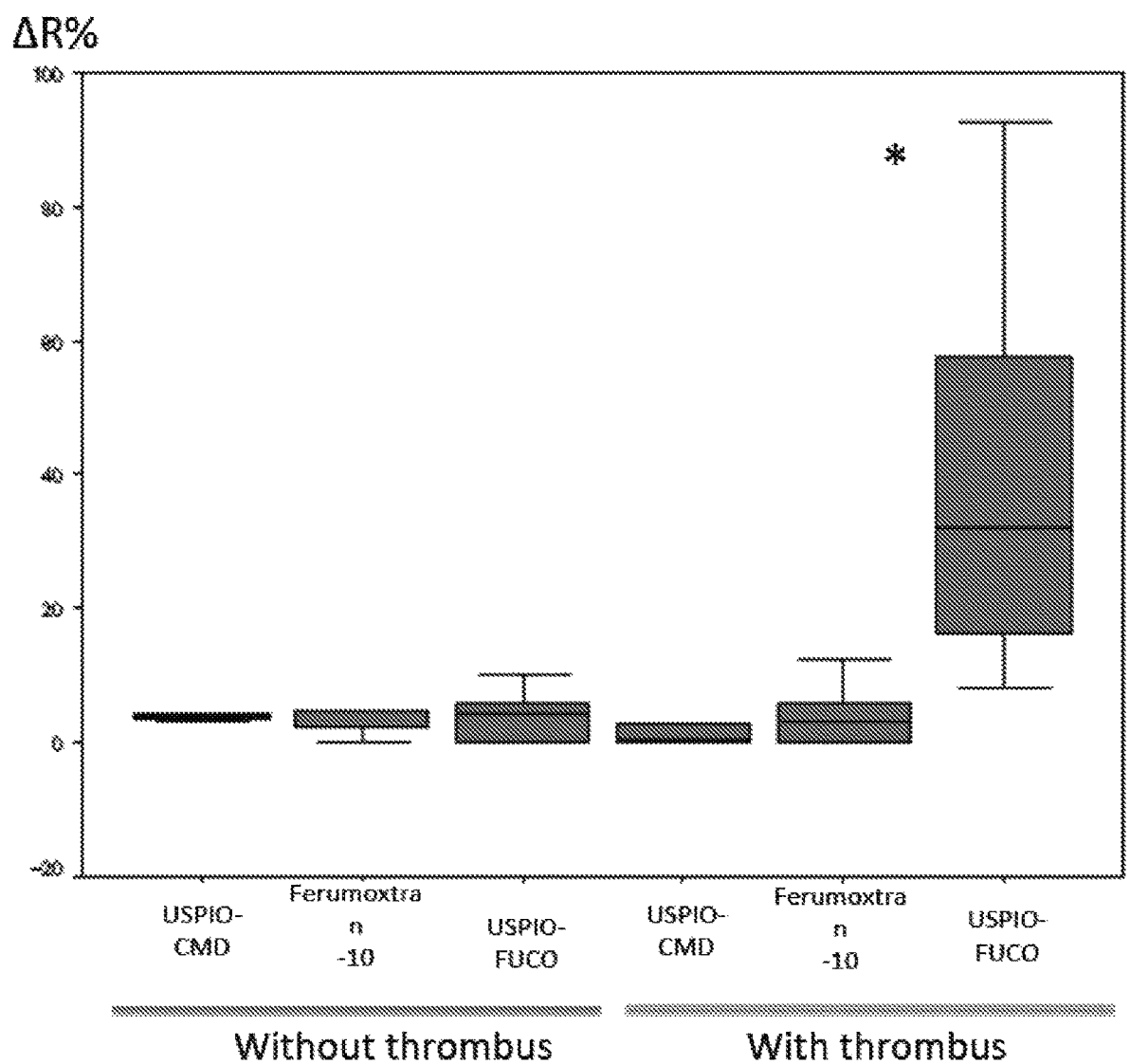
Figure 12B:
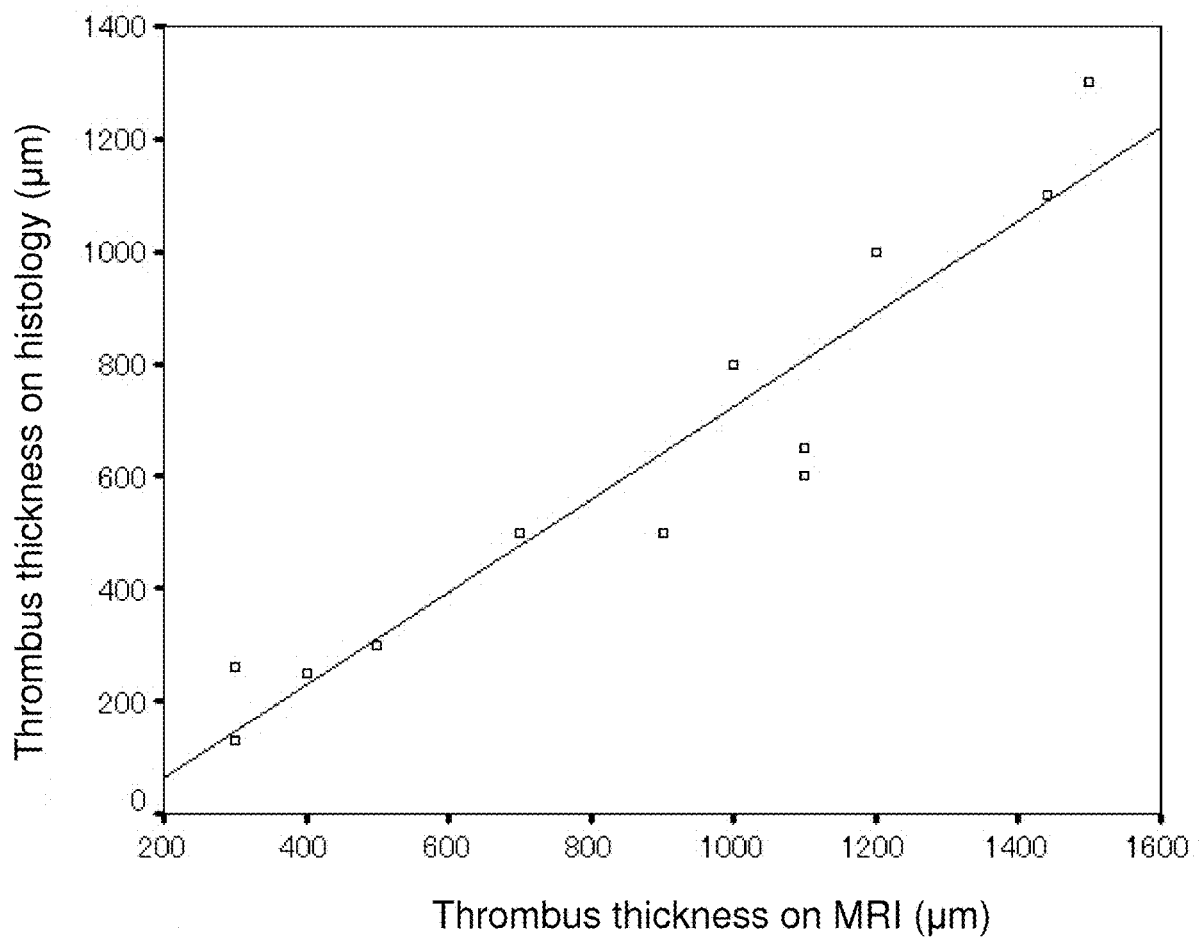

FIG. 12(A) shows the effects of different contrast agents on aorta with or without thrombus measured by MRI 60 minutes after injection. At the site of thrombus, the Group that had received USPIO-FUCO showed significantly strong area reduction compared to the Group that had received USPIO-CMD (p<0.001). In aorta without thrombus, there was no significant luminal reduction irrespective of the contrast agents used. Cf. Thrombus (−) group; CMD, 3.88±0.23: FUCO, 3.89±0.88, Thrombus (+) group; CMD, 1.15±0.48: FUCO, 38.53±24. FIG. 12(B) shows a scatter plot of thrombus thickness measured by MR Imaging and by histology. A strong correlation was observed, ($r^2$=0.90) between the two methods with consistent overestimation of ILT thickness using MRI. Thickness on histology=−103.79−0.83×Thickness on MR.

Figure 13:
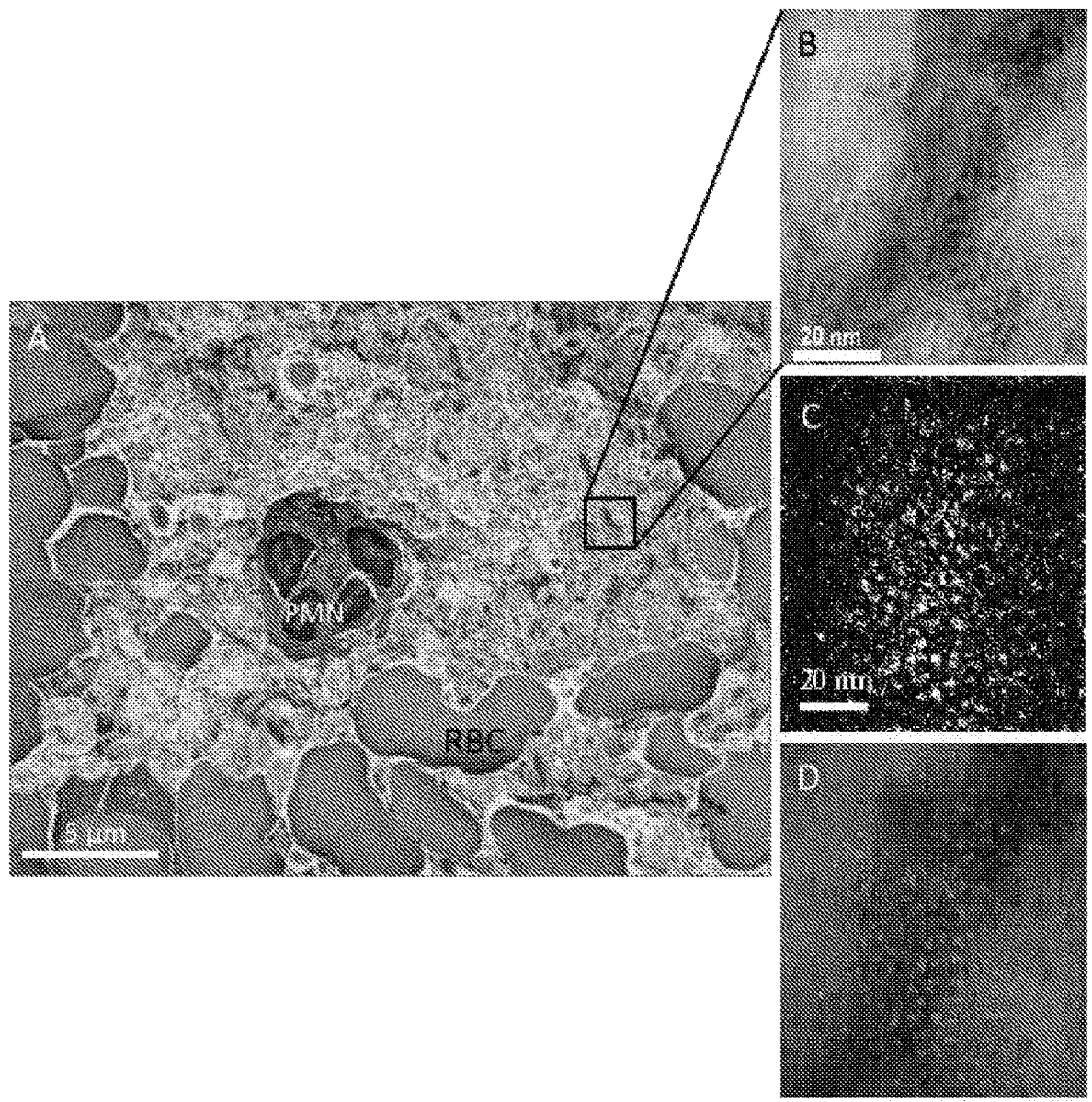

FIG. 13 shows a confirmation of histological data by electron microscopy. TEM confirmed the histological data showing (A) areas of platelet/fibrin-rich material and hemagglutination areas in which Red Blood Cell (RBC) predominated. PolyNuclear Neutrophils (PNNs) predominated in platelet/fibrin-rich areas. Hyperdense iron signal predominated in platelet/fibrin areas (square). The presence of iron was confirmed by more powerful enlargement (B, TEM image), Iron energy filtered TEM (EFTEM) evidencing iron cores in white (C) and (D) (merged image).

DEFINITIONS

Throughout the specification, several terms are employed that are defined in the following paragraphs.

As used herein, the term "selectin" has its art understood meaning and refers to any member of the family of carbohydrate-binding, calcium-dependent cell adhesion molecules that are constitutively or inductively present on the surface of leukocytes, endothelial cells or platelets. The term "E-selectin", as used herein, has its art understood meaning and refers to the cell adhesion molecule also known as SELE, CD62E, ELAM, ELAM1, ESEL, or LECAM2 (Genbank Accession Numbers for human E-selectin: NM_000450 (mRNA) and NP_000441 (protein)). As used herein, the term "L-selectin" has its art understood meaning and refers to the cell adhesion molecule also known as SELL, CD62L, LAM-1, LAM1, LECAM1, LNHR, LSEL, LYAM1, Leu-8, Lyam-1, PLNHR, TQ1, or hLHRc (Genbank Accession Numbers for human L-selectin: NM_000655 (mRNA) and NP_000646 (protein)). The term "P-selectin", as used herein, has its art understood meaning and refers to the cell adhesion molecule also known as a SELP, CD62, CD62P, FLJ45155, GMP140, GRMP, PADGEM, or PSEL (Genbank Accession Numbers for human P-selectin: NM_003005 (mRNA) and NP_002996 (protein)).

As used herein, the term "imaging agent" refers to a compound that can be used to detect specific biological elements (e.g., biomolecules) using imaging techniques. Imaging agents of the invention are molecules comprising at least one fucoidan moiety associated with at least one detectable moiety. Imaging agents of the present invention can be used to detect selectins in in vitro and ex vivo biological systems as well as in subjects.

The term "fucoidan moiety" refers to any fucoidan entity exhibiting high affinity, specificity and/or selectivity for selectins. In the context of the present invention, when a fucoidan moiety is part of a molecule (e.g., an imaging agent), it confers its specificity/selectivity/affinity properties to the molecule, and the molecule becomes "selectin-targeted" (i.e., the molecule specifically and/or efficiently interacts with and/or binds to selectins).

The terms "binding affinity" and "affinity" are used herein interchangeably and refer to the level of attraction between molecular entities. Affinities can be expressed quantitatively as a dissociation constant ($K_d$ or $K_D$), or its inverse, the association constant ($K_a$ or $K_A$).

The term "detectable moiety", as used herein refers to any entity which, when part of a molecule, allows visualization of the molecule, for example using imaging techniques.

The terms "pathological condition associated with selectins", "disease associated with selectins" and "disorder associated with selectins" are used herein interchangeably. They refer to any disease condition characterized by undesirable or abnormal selectin-mediated interactions. Such conditions include, for example, disease conditions associated with or resulting from the homing of leukocytes to sites of inflammation, the normal homing of lymphocytes to secondary lymph organs, the interaction of platelets with activated endothelium, platelet-platelet and platelet-leukocyte interactions in the blood vascular compartment, and the like. Examples of such disease conditions include, but are not limited to, tissue transplant rejection, platelet-mediated diseases (e.g., atherosclerosis and clotting), hyperactive coronary circulation, acute leukocyte-mediated lung injury (e.g., adult respiratory distress syndrome—ARDS), Crohn's disease, inflammatory diseases (e.g., inflammatory bowel disease), autoimmune diseases (e.g., multiple sclerosis, myasthenia gravis), infection, cancer (including metastasis), thrombosis, wounds and wound-associated sepsis, burns, spinal cord damage, digestive tract mucous membrane disorders (e.g., gastritis, ulcers), osteoporosis, rheumatoid arthritis, osteoarthritis, asthma, allergy, psoriasis, septic shock, stroke, nephritis, atopic dermatitis, frostbite injury, adult dysponoea syndrome, ulcerative colitis, systemic lupus erythematosus, diabetes and reperfusion injury following ischemic episodes.

As used herein, the term "subject" refers to a human or another mammal (e.g., mouse, rat, rabbit, hamster, dog, cat, cattle, swine, sheep, horse or primate). In many embodiments, the subject is a human being. In such embodiments, the subject is often referred to as an "individual", or to a "patient" if the subject is afflicted with a disease or clinical condition. The terms "subject", "individual" and "patient" do not denote a particular age, and thus encompass adults, children and newborns.

The term "biological sample" is used herein in its broadest sense. A biological sample is generally obtained from a subject. A sample may be of any biological tissue or fluid that can produce and/or contain selectins. Frequently, a sample will be a "clinical sample", i.e., a sample derived from a patient. Such samples include, but are not limited to, bodily fluids which may or may not contain cells, e.g., blood, urine, saliva, cerebrospinal fluid (CSF), synovial fluid, tissue or fine needle biopsy samples, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample, proteins or other molecules extracted from the sample. Processing of a biological sample may involve one or more of: filtration, distillation, extraction, concentration, inactivation of interfering components, addition of reagents, and the like.

The term "effective amount", when used herein in reference to a selectin-targeted imaging agent of the invention, or a pharmaceutical composition thereof, refers to any amount of the imaging agent, or pharmaceutical composition, which is sufficient to fulfill its intended purpose(s) (e.g., the purpose may be the detection and/or imaging of selectins present in a biological system or in a subject, and/or the diagnosis of a disease associated with selectins).

A "pharmaceutical composition", as used herein, is defined as comprising at least one selectin-targeted imaging agent, or a physiological tolerable salt thereof, and at least one pharmaceutically acceptable carrier.

The term "physiologically tolerable salt" refers to any acid addition or base addition salt that retains the biological activity and properties of the free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the like). Base addition salts can be formed with inorganic bases (e.g., sodium, potassium, lithium, ammonium, calcium, magnesium, zinc, aluminum salts, and the like) and organic bases (e.g., salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like).

As used herein, the term "pharmaceutically acceptable carrier" refers to a carrier medium which does not interfere with the effectiveness of the biological activity of the active ingredients and which is not excessively toxic to the hosts at the concentrations at which it is administered. The term includes solvents, dispersion media, coatings, antibacterial and antifungal agents, isotonic agents, adsorption delaying agents, and the like. The use of such media and agents for pharmaceutically active substances is well known in the art (see, for example, Remington's Pharmaceutical Sciences, E. W. Martin, 18$^{th}$ Ed., 1990, Mack Publishing Co., Easton, Pa.).

The term "treatment" is used herein to characterize a method or process that is aimed at (1) delaying or preventing the onset of a disease or condition (e.g., a selectin-associated state or condition); (2) slowing down or stopping the progression, aggravation, or deterioration of the symptoms of the state or condition; (3) bringing about amelioration of the symptoms of the state or condition; and/or (4) curing the state or condition. A treatment may be administered prior to the onset of the disease, for a prophylactic or preventive action. Alternatively or additionally, a treatment may be administered after initiation of the disease or condition, for a therapeutic action.

The terms "approximately" and "about", as used herein in reference to a number, generally include numbers that fall within a range of 10% in either direction of the number (greater than or less than the number) unless otherwise stated or otherwise evident from the context (except where such a number would exceed 100% of a possible value).

DETAILED DESCRIPTION OF CERTAIN PREFERRED EMBODIMENTS

As mentioned above, the present invention is directed to the use of fucoidans for the imaging of selectins and the diagnosis of pathophysiological conditions associated with selectins. In particular, the invention encompasses imaging agents, kits and strategies for specifically detecting the presence of selectins in vitro, ex vivo as well as in vivo using imaging techniques.

I—Selectin-Targeted Imaging Agents

In one aspect, the invention relates to a new class of imaging agents that have high affinity and specificity for selectins. More specifically, selectin-targeted imaging agents are provided that comprise at least one fucoidan moiety associated with at least one detectable moiety.

Fucoidan Moieties

Fucoidans (also called fucosans or sulfated fucans) are sulfated polysaccharides with a wide spectrum of biological activities, including anticoagulant, antithrombotic, antivirus, antitumor, immunomodulatory, anti-inflammatory, and antioxidant activities (B. Li et al., Molecules, 2008, 13: 1671-1695; D. Logeart et al., J. Biomed. Mater Res., 1996, 30: 501-508). Fucoidans are found mainly in various species of brown seaweed (B. Li et al., Molecules, 2008, 13: 1671-1695; M. Kusaykin et al., Biotechnol. J., 2008, 3: 904-915). Variant forms of fucoidans have also been found in marine animal species, including the sea cucumber. Thus, compared to other sulfated polysaccharides, fucoidans are widely available from various kinds of cheap sources, and easily obtained using methods of extraction known in the art (C. Colliec et al., Phytochemistry, 1994, 35(3): 697-700). These methods of extraction generally yield fucoidans with molecular weights in the 70-800 kDa range. Processes have also been developed to prepare low molecular weight fucoidans from high molecular weight fucoidans, e.g., lower than about 20 kDa (EP 0 403 377B, U.S. Pat. No. 5,321,133), or lower than about 10 kDa (EP 0 846 129 B; U.S. Pat. No. 6,028,191; A. Nardella et al., Carbohydr. Res., 1996, 289: 201-208).

Fucoidans are $\alpha$-1,2- or $\alpha$-1,3-linked L-fucose polymers that are sulfated on position 4 and position 2 or 3 following the glycosidic linkage. However, besides fucose and sulfate residues, fucoidans also contain other monosaccharides (e.g., mannose, galactose, glucose, xylose, etc) and uronic acid groups. It is known in the art that the structure of fucoidans from different brown algae varies from species to species. Furthermore, the structure of fucoidans can also be chemically modified. For example, methods have been developed to increase the percentage of sulfate groups of fucoidans in order to obtain oversulfated fucoidans or fucoidan fragments (T. Nishino et al., Carbohydr. Res., 1992, 229: 355-362; S. Soeda et al., Thromb. Res., 1993, 72: 247-256).

Fucoidan moieties suitable for use in the present invention are fucoidan moieties that have some degree of attraction for selectins and can play a targeting role when comprised in an imaging agent. Preferably, fucoidan moieties are stable, non-toxic entities that retain their affinity/specificity/selectivity properties under in vitro and in vivo conditions. In preferred embodiments, fucoidan moieties exhibit high affinity and specificity for selectins, i.e., they specifically and efficiently interact with, bind to, or associate with selectins. Suitable fucoidan moieties include fucoidans that exhibit affinity and specificity for only one of the selectins (i.e., for L-selectin, E-selectin or P-selectin) as well as fucoidans that exhibit affinity and specificity for more than one selectin, including those moieties which can efficiently interact with, bind to or associate with all three selectins. Preferably, the interaction between a selectin and a fucoidan moiety within an imaging agent is strong enough for at least the time necessary for selectin detection using an imaging technique. In certain embodiments, a suitable fucoidan moiety interacts with a selectin, preferably a human selectin, with a dissociation constant ($K_d$) between about 0.1 nM and about 500 nM, preferably between about 0.5 nM and about 10 nM, more preferably between about 1 nM and about 5 nM.

The design of an inventive imaging agent will be dictated by its intended purpose(s) and the properties that are desirable in the particular context of its use. Thus, fucoidan moieties will be chosen based on their known, observed or expected, properties. For example, in embodiments where an imaging agent of the invention is to be used in the diagnosis of neurodegenerative disorders characterized by undesirable or abnormal selectin-mediated interactions in the brain, the imaging agent will preferably be capable of crossing the blood-brain barrier. Therefore, such an imaging agent will preferably contain a fucoidan moiety of low molecular weight (e.g., 2-8 kDa or lower than 5 kDa). In contrast, an imaging agent containing a fucoidan moiety of high molecular weight will be suited for situations in which the agent is to be used, for example to image selectins in the vascular system. Indeed, because of its high molecular weight, the imaging agent will not be able to easily diffuse and will therefore more likely remain within the vascular system, thereby allowing a more selective targeting of the system of interest.

A fucoidan moiety of high molecular weight can also have the advantage of being able to carry a high number of detectable moieties, thus increasing the sensibility of the imaging agent (i.e., allowing the detection of lower concentrations of selectins). In addition to their molecular weight, fucoidan moieties may be selected based on their sulfate content. By varying the sulfate content (either by selection of naturally-occurring fucoidans or by chemical modification), it may be possible to modulate the specificity of the fucoidan moiety (and corresponding imaging agent) for one of the selectins (L-selectin, E-selectin or P-selectin). It is known, for example, that binding to P- and E-selectins increases with the presence of sulfate groups on the ligand (T. V. Pochechueva et al., Bioorganic & Medicinal Chemistry Letters, 2003, 13: 1709-1712).

Alternatively or additionally, a fucoidan moiety may be selected based on its structure and, in particular, based on the presence of at least one functional group that can be used (or that can be easily chemically converted to a different functional group that can be used) to associate the fucoidan moiety to a detectable moiety. Examples of suitable functional groups include, but are not limited to, carboxy groups, thiols, amino groups (preferably primary amines), and the like.

Detectable Moieties

In the context of the present invention, detectable moieties are entities that are detectable by imaging techniques such as ultrasonography, Magnetic Resonance Imaging (MRI), Positron Emission Tomography (PET), Single Photon Emission Computed Tomography (SPECT), fluorescence spectroscopy, Computed Tomography, X-ray radiography, or any combination of these techniques. Preferably, detectable moieties are stable, non-toxic entities which, when part of a selectin-targeted imaging agent, retain their properties under in vitro and in vivo conditions.

Radioactive Imaging Moieties.

In certain embodiments, the selectin-targeted imaging agent is designed to be detectable by a nuclear medicine imaging techniques such as planar scintigraphy (PS), Positron Emission Tomography (PET) and Single Photon Emission Computed Tomography (SPECT). In such embodiments, the imaging agent of the invention comprises at least one fucoidan moiety associated with at least one radionuclide (i.e., a radioactive isotope).

SPECT and PET have been used to detect tumors, aneurysms, irregular or inadequate blood flow to various tissues, blood cell disorders, and inadequate functioning of organs, such as thyroid and pulmonary function deficiencies. Both techniques acquire information on the concentration of radionuclides introduced into a biological sample or a patient's body. PET generates images by detecting pairs of gamma rays emitted indirectly by a positron-emitting radionuclide. A PET analysis results in a series of thin slice images of the body over the region of interest (e.g., brain, breast, liver). These thin slice images can be assembled into a three dimensional representation of the examined area. However, there are only few PET centers because they must be located near a particle accelerator device that is required to produce the short-lived radioisotopes used in the technique. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Planar scintigraphy (PS) is similar to SPECT in that it uses the same radionuclides. However, PS only generates 2D-information.

Thus, in certain embodiments, the at least one detectable moiety in an imaging agent of the invention is a radionuclide detectable by PET. Examples of such radionuclides include carbon-11 ($^{11}C$), nitrogen-13 ($^{13}N$), oxygen-15 ($^{15}O$) and fluorine-18 ($^{18}F$).

In other embodiments, the detectable moiety is a radionuclide detectable by planar scintigraphy or SPECT. Examples of such radionuclides include technetium-99m ($^{99m}Tc$), gallium-67 ($^{67}Ga$), yttrium-91 ($^{91}Y$), indium-111 ($^{111}In$), rhenium-186 ($^{186}Re$), and thallium-201 ($^{201}Tl$). Preferably, the radionuclide is technetium-99m ($^{99m}Tc$). Over 85% of the routine nuclear medicine procedures that are currently performed use radiopharmaceutical methodologies based on $^{99m}Tc$. Therefore, in certain preferred embodiments, the at least one detectable moiety of an imaging agent is $^{99m}Tc$.

MRI Imaging Moieties.

In certain embodiments, the selectin-targeted imaging agent is designed to be detectable by Magnetic Resonance Imaging (MRI). MRI, which is an application of Nuclear Magnetic Resonance (NMR), has evolved into one of the most powerful non-invasive techniques in diagnostic clinical medicine and biomedical research. It is widely used as a non-invasive diagnostic tool to identify potentially maleficent physiological anomalies, to observe blood flow or to determine the general status of the cardiovascular system. MRI has the advantage (over other high-quality imaging methods) of not relying on potentially harmful ionizing radiation.

Thus, in certain embodiments, an imaging agent of the invention comprises at least one fucoidan moiety associated with at least one paramagnetic metal ion. Examples of paramagnetic metal ions detectable by MRI are gadolinium III ($Gd^{3+}$), chromium III ($Cr^{3+}$), dysprosium III ($Dy^{3+}$), iron III ($Fe^{3+}$), manganese II ($Mn^{2+}$), and ytterbium III ($Yb^{3+}$). In certain preferred embodiments, the paramagnetic metal ion is gadolinium III ($Gd^{3+}$). Gadolinium is an FDA-approved contrast agent for MRI.

In other embodiments, the imaging agent of the invention comprises at least one fucoidan moiety associated with at least one ultrasmall superparamagnetic iron oxide (USPIO) particle. USPIO particles are currently under investigation as contrast agents for imaging human pathologies (C. Corot et al., Adv. Drug Deliv. Rev., 2006, 56: 1472-1504). They are composed of a crystalline iron oxide core containing thousands of iron atoms which provide a large disturbance of the Magnetic Resonance signal of surrounding water. In contrast to other types of nanoparticles such as quantum dots (currently under investigation as extremely sensitive fluorescent probes), USPIO particles exhibit a very good biocompatibility. Chemical coating of USPIO particles is required to ensure their dispersion in biological media. The presence of an appropriate coating may also result in a decrease in the clearance of the particles ("stealth" effect) and may provide a means to bind these particles to molecules that are able to target a specific tissue (R. Weissleder et al., Magn. Reson. Q, 1992, 8: 55-63). Polysaccharides, such as dextran and its carboxymethylated derivatives, are currently used as coatings.

USPIO particles are known in the art and have been described (see, for example, J. Petersein et al., Magn. Reson. Imaging Clin. Am., 1996, 4: 53-60; B. Bonnemain, J. Drug Target, 1998, 6: 167-174; E. X. Wu et al., NMR Biomed., 2004, 17: 478-483; C. Corot et al., Adv. Drug Deliv. Rev., 2006, 58: 1471-1504; M. Di Marco et al., Int. J. Nanomedicine, 2007, 2: 609-622). USPIO particles are commercially available, for example, from AMAG Pharmaceuticals, Inc. under the tradenames Sinerem® and Combidex®.

The present invention proposes to coat USPIO particles with fucoidan moieties and use the resulting imaging agents to detect selectins by MRI. Such inventive imaging agents may be particularly useful in the diagnosis of cardiovascular pathologies associated with selectins. Indeed, with a radius of about 15 nm, USPIO particles are likely to diffuse only weakly outside the vascular space with the exception of more permeable pathological vascular tissues such as atherosclerotic walls. Therefore, they constitute a good blood pool agent (J. Bremerich et al., Eur. Radiol., 2007, 17: 3017-3024).

The present Applicants have developed USPIO-fucoidan nanoparticles that proved to be efficient at detecting, by MRI, platelet-rich thrombus with high sensitivity and specificity (see Example 6). The nanoparticles developed by the Applicants have a mean diameter of about 65 mm and exhibit a core-shell structure, where the fucoidan moieties constitute the outer shell of the particles. Consequently, the present invention provides an MR imaging agent under the form of USPIO particles associated with fucoidan moieties. In certain embodiments, the fucoidan moieties have an average molecular weight of about 2000 to about 9000 Da, e.g., about 5000, about 6000, about 7000 or about 8000 Da. In other embodiments, the fucoidan moieties have an average molecular weight of about 10,000 to about 90,000 Da, e.g., about 20,000, about 30,000, about 40,000, about 50,000, about 60,000, about 70,000 or about 80,000 Da. In yet other embodiments, the fucoidan moieties have an average molecular weight of about 100,000 to about 500,000 Da. Preferably, USPIO-fucoidan nanoparticles according to the present invention will be prepared such that the USPIOs are coated with fucoidan moieties and the resulting nanoparticles have a core-shell structure, the outer shell being constituted by the fucoidan moieties. In certain embodiments, a USPIO-fucoidan nanoparticle according to the invention has a mean diameter between about 15 and about 100 nm, preferably between about 40 and about 80 nm, more preferably between about 50 and about 70 nm.

Contrast-Enhanced Ultrasonography Imaging Moieties.

In certain embodiments, the selectin-targeted imaging agent is designed to be detectable by contrast-enhanced ultrasonography (CEUS). Ultrasound is a widespread technology for the screening and early detection of human diseases. It is less expensive than MRI or scintigraphy and safer than molecular imaging modalities such as radionuclide imaging because it does not involve radiation.

Thus, in certain embodiments, the imaging agent of the invention comprises at least one fucoidan moiety associated with at least one acoustically active (gas-filled) microbubble. A variety of acoustically active microbubbles may be used in the practice of the present invention (A. L. Klibanov, Bioconj. Chem., 2005, 16: 9-17; J. R. Lindner, Nat. Rev. Drug Discov., 2004, 3: 527-532; M. McCulloch et al., J. Am. Soc. Echocardiogr., 2000, 13: 959-967; A. M. Takalkar et al., J. Contr. Release, 2004, 96: 473-482; G. E. Weller et al., Biotechnol. Bioeng., 2005, 92: 780-788).

Generally, such microbubbles are comprised of a gas core and a shell. The gas core is the most important part of the microbubble because it allows detection. When gas bubbles are caught in an ultrasonic frequency field, they compress, oscillate and reflect a characteristic echo, which generates a strong and unique sonogram in CEUS. Gas cores can be composed of air, or heavy gases such as perfluorocarbon or nitrogen. Microbubbles with heavy gas-cores are likely to last longer in the circulation compared to microbubbles with air-comprising cores. The shell material determines how easily the microbubble is taken up by the immune system. A microbubble with a shell made of a more hydrophilic material tends to be taken up more easily by the immune system, while a more hydrophobic shell material tends to increase the microbubble residence time in the circulation, thus increasing the time available for contrast imaging. Microbubbles shells may be made of albumin, galactose, lipids or polymers (J. R. Lindner, Nat. Rev. Drug Discov., 2004, 3: 527-532). Regardless of the shell or gas core composition, microbubble size is fairly uniform. Their diameter is generally in the 1-4 micrometer range. Therefore, they are smaller than red blood cells, allowing them to flow easily through the circulation as well as the microcirculation (F. S. Vallanueva et al., Nat. Clin. Pract. Cardiovasc. Med., 2008, 5 Suppl. 2: S26-S32).

In other embodiments, the imaging agent of the invention comprises at least one fucoidan moiety associated with at least one acoustically active lipid particle (i.e., a gas-filled liposome). A variety of acoustically active lipid particles are known in the art and may be used in the practice of the present invention (H. Alkan-Onyuksel et al., J. Pharm. Sci., 1996, 85: 486-490; S. M. Demos et al., J. Am. Coll. Cardiol., 1999, 33: 867-875; S. L. Huang et al., J. Pharm. Sci., 2001, 90: 1917-1926; S. L. Huang et al., J. Ultrasound Med., 2002, 28: 339-348; A. Hamilton et al., Circulation, 2002, 105: 2772-2778).

Fluorescence Imaging Moieties.

In certain embodiments, the selectin-targeted imaging agent is designed to be detectable by fluorescence spectroscopy. In such embodiments, the imaging agents of the invention comprises at least one fucoidan moiety associated with at least one fluorescent moiety.

Favorable optical properties of fluorescent moieties to be used in the practice of the present invention include high molecular absorption coefficient, high fluorescence quantum yield, and photostability. Preferred fluorescent moieties exhibit absorption and emission wavelengths in the visible (i.e., between 400 and 700 nm) or the near infra-red (i.e., between 700 and 950 nm). Selection of a particular fluorescent moiety will be governed by the nature and characteristics of the illumination and detection systems used in the diagnostic method. In vivo fluorescence imaging uses a sensitive camera to detect fluorescence emission from fluorophores in whole-body living mammals. To overcome the photon attenuation in living tissue, fluorophores with emission in the near-infrared (NIR) region are generally preferred (J. Rao et al., Curr. Opin. Biotechnol., 2007, 18: 17-25). The list of NIR probes continues to grow with the recent addition of fluorescent organic, inorganic and biological nanoparticles. Recent advances in imaging strategies and reporter techniques for in vivo fluorescence imaging include novel approaches to improve the specificity and affinity of the probes, and to modulate and amplify the signal at target sites for enhanced sensitivity. Further emerging developments are aiming to achieve high-resolution, multimodality and lifetime-based in vivo fluorescence imaging.

Numerous fluorescent moieties with a wide variety of structures and characteristics are suitable for use in the practice of the present invention. Suitable fluorescent labels include, but are not limited to, quantum dots (i.e., fluorescent inorganic semiconductor nanocrystals) and fluorescent dyes such as Texas red, fluorescein isothiocyanate (FITC), phycoerythrin (PE), rhodamine, fluorescein, carbocyanine, Cy-3™ and Cy-5™ (i.e., 3- and 5-N,N'-diethyltetra-methylindodicarbocyanine, respectively), Cy5.5, Cy7, DY-630, DY-635, DY-680, and Atto 565 dyes, merocyanine, styryl dye, oxonol dye, BODIPY dye (i.e., boron dipyrromethene difluoride fluorophore), and analogues, derivatives or combinations of these molecules.

In certain embodiments, the detectable moiety is detectable by time-resolved fluorometry. For example, the detectable moiety is europium ($Eu^{3+}$).

As will be understood by one skilled in the art, the selection of a particular type of detectable moiety in the design of a selectin-targeted imaging agent will be dictated by the intended purpose of the imaging agent as well as by the imaging technique to be used in the detection.

In certain embodiments, an imaging agent of the present invention may be designed to be detectable by more than one imaging technique, for example by a combination of MRI-PET, MRI-SPECT, fluorescence-MRI, X-ray radiography-scintigraphy, and the like. Multimodal imaging provides different types of information about biological tissues, such as both structural and functional properties. Thus, for example, an imaging agent according to the present invention may comprise at least one fucoidan moiety associated with at least one detectable moiety that is detectable by more than one imaging technique. Examples of such detectable moieties include, but are not limited to, europium, which is fluorescent and detectable by MRI; and luminescent hybrid nanoparticles with a paramagnetic $Gd_2O_3$ core that are developed as contrast agents for both in vivo fluorescence and MRI (J. L; Bridot et al., J. Am. Chem. Soc., 2007, 129: 5076-5084) Alternatively, an imaging agent may comprise at least one fucoidan moiety associated with a first detectable moiety and a second detectable moiety, wherein the first detectable moiety is detectable by a first imaging technique and the second detectable moiety is detectable by a second imaging technique. A large variety of imaging agents with double detectability may thus be obtained. The simultaneous use of two different imaging agents (i.e., of a first imaging agent detectable by a first imaging technique and a second imaging agent detectable by a second imaging technique) is also contemplated.

Synthesis of Selectin-Targeted Imaging Agents

The inventive imaging agents may be prepared by any synthetic method known in the art, the only requirement being that, after reaction, the fucoidan moiety and detectable moiety retain their affinity and detectability property, respectively. The fucoidan and detectable moieties may be associated in any of a large variety of ways. Association may be covalent or non-covalent. When the association is covalent, the fucoidan and detectable moieties may be bound to each other either directly or indirectly (e.g., through a linker). When the detectable moiety is a metal entity, the fucoidan moiety may be associated to the detectable metal entity via a metal-chelating moiety.

More specifically, in certain embodiments, the fucoidan moiety and detectable moiety are directly covalently linked to each other. The direct covalent binding can be through an amide, ester, carbon-carbon, disulfide, carbamate, ether, thioether, urea, amine or carbonate linkage. The covalent binding can be achieved by taking advantage of functional groups present on the fucoidan moiety and detectable moieties. Suitable functional groups that can be used to attach the two moieties together include, but are not limited to, amines (preferably primary amines), anhydrides, hydroxy groups, carboxy groups and thiols. A direct linkage may also be formed by using an activating agent, such as a carbodiimide, to bind, for example, the primary amino group present on one moiety to the carboxy group present on the other moiety. Activating agents suitable for use in the present invention are well known in the art.

In other embodiments, the fucoidan moiety and detectable moiety are indirectly covalently linked to each other via a linker group. This can be accomplished by using any number of stable bifunctional agents well known in the art, including homofunctional and heterofunctional linkers. The use of a bifunctional linker differs from the use of an activating agent in that the former results in a linking moiety being present in the inventive imaging agent after reaction, whereas the latter results in a direct coupling between the two moieties involved in the reaction. The main role of the bifunctional linker is to allow the reaction between two otherwise chemically inert moieties. However, the bifunctional linker, which becomes part of the reaction product, can also be selected such that it confers some degree of conformational flexibility to the imaging agent (e.g., the bifunctional linker may comprise a straight alkyl chain containing several atoms).

A wide range of suitable homofunctional and heterofunctional linkers known in the art can be used in the context of the present invention. Preferred linkers include, but are not limited to, alkyl and aryl groups, including straight chain and branched alkyl groups, substituted alkyl and aryl groups, heteroalkyl and heteroaryl groups, that have reactive chemical functionalities such as amino, anhydride, hydroxyl, carboxyl, carbonyl groups, and the like.

Methods of direct or indirect covalent association may be used, for example, in the synthesis of selectin-targeted imaging agents comprising a fluorescent moiety. Similarly, such methods may be employed for the coating of USPIO particles by fucoidan moieties (see Example 3), or to graft fucoidan onto acoustically active microbubbles or liposomes (see Example 4).

In other embodiments, the fucoidan moiety and the detectable moiety are directly but non-covalently associated to each other. Non-covalent associations include, but are not limited to, hydrophobic interactions, electrostatic interactions, dipole interactions, van der Waals interactions, and hydrogen bonding. For example, a fucoidan moiety and a detectable metal entity may be associated by complexation. Suitable complexation methods include, for example, direct incorporation of the metal entity into the fucoidan moiety and transmetallation. When possible, direct incorporation is preferred. In such a method, an aqueous solution of the fucoidan moiety is generally exposed to or mixed with a metal salt. The pH of the reaction mixture may be between about 4 and about 11. Direct incorporation methods are well known in the art and different procedures have been described (see, for example, WO 87/06229). The present Applicants have shown that a low molecular weight fucoidan can easily be complexed to technetium-99m (see Example 2). A method of transmetallation is used when the metal entity needs to be reduced to a different oxidative state before incorporation. Transmetallation methods are well known in the art. It is to be understood that, given the short lifetime of certain radionuclides (e.g., $^{99m}$Tc), the direct incorporation may have to be performed shortly prior to the use of the imaging agent.

When direct, non-covalent association between the fucoidan and detectable metal moieties is not possible, the selectin-targeted imaging agent may comprise at least one fucoidan moiety associated with at least one detectable moiety, wherein the detectable moiety comprises a metal-chelating moiety complexed to a detectable metal moiety. The association between the fucoidan moiety and the metal-chelating moiety is preferably covalent. Suitable metal-chelating moieties for use in the present invention may be any of a large number of metal chelators and metal complexing molecules known to bind detectable metal moieties. Preferably, metal-chelating moieties are stable, non-toxic entities that bind radionuclides or paramagnetic metal ions with high affinity.

Examples of metal-chelating moieties that have been used for the complexation of paramagnetic metal ions, such as gadolinium III ($Gd^3$), include DTPA (diethylene triamine-pentaacetic acid); DOTA (1,4,7,10-tetraazacyclododecane-N,N',N'',N'''-tetraacetic acid); and derivatives thereof (see, for example, U.S. Pat. Nos. 4,885,363; 5,087,440; 5,155, 215; 5,188,816; 5,219,553; 5,262,532; and 5,358,704; and D. Meyer et al., Invest. Radiol. 1990, 25: S53-55), in particular, DTPA-bis(amide) derivatives (U.S. Pat. No. 4,687,659). Other metal-chelating moieties that complex paramagnetic metal ions include acyclic entities such as aminopolycarboxylic acids and phosphorus oxyacid analogues thereof (e.g., triethylenetetraminehexaacetic acid or TTHA), and dipyridoxal diphosphate (DPDP) and macrocyclic entities (e.g., 1,4,7,10-tetraazacyclododecane-N,N', N''-triacetic acid or DO3A). Metal-chelating moieties may also be any of the entities described in U.S. Pat. Nos. 5,410,043; 5,277,895; and 6,150,376; or in F. H. Arnold, Biotechnol. 1991, 9: 151-156.

Examples of metal-chelating moieties that complex radionuclides, such as technetium-99m, include, for example, $N_2S_2$ and $N_3S$ chelators (A. R. Fritzberg et al., J. Nucl. Med. 1982, 23: 592-598; U.S. Pat. Nos. 4,444,690; 4,670,545; 4,673,562; 4,897,255; 4,965,392; 4,980,147; 4,988,496; 5,021,556 and 5,075,099). Other suitable metal-chelating moieties can be selected from polyphosphates (e.g., ethylene diaminetetramethylenetetra-phosphonate, EDTMP); aminocarboxylic acids (e.g., EDTA, N-(2-hydroxy)ethylene-diaminetriacetic acid, nitrilotriacetic acid, N,N-di(2-hydroxyethyl)glycine, ethylenebis(hydroxyphenylglycine) and diethylenetriamine pentaacetic acid); 1,3-diketones (e.g., acetylacetone, trifluoroacetylacetone, and thenoyltrifluoroacetone); hydroxycarboxylic acids (e.g., tartaric acid, citric acid, gluconic acid, and 5-sulfosalicylic acid); polyamines (e.g., ethylenediamine, diethylenetriamine, triethylenetetramine, and triaminotriethylamine); aminoalcohols (e.g., triethanolamine and N-(2-hydroxyethyl)ethylenediamine); aromatic heterocyclic bases (e.g., 2,2'-diimidazole, picoline amine, dipicoline amine and 1,10-phenanthroline); phenols (e.g., salicylaldehyde, disulfopyrocatechol, and chromotropic acid); aminophenols (e.g., 8-hydroxyquinoline and oximesulfonic acid); oximes (e.g., hexamethylpropyleneamine oxime, HMPAO); Schiff bases (e.g., disalicylaldehyde 1,2-propylenediamine); tetrapyrroles (e.g., tetraphenylporphine and phthalocyanine); sulfur compounds (e.g., toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea); synthetic macrocyclic compounds (e.g., dibenzo[18]crown-6), or combinations of two or more of the above agents.

As can readily be appreciated by those skilled in the art, a selectin-targeted imaging agent of the invention can comprise any number of fucoidan moieties and any number of detectable moieties, linked to one another by any number of different ways. The fucoidan moieties within an inventive imaging agent may be all identical or different. Similarly, the detectable moieties within an inventive imaging agent may be all identical or different. The precise design of a selectin-targeted imaging agent will be influenced by its intended purpose(s) and the properties that are desirable in the particular context of its use II—Uses of Selectin-Targeted Imaging Agents The invention provides reagents and strategies to image and detect the presence of selectins. More specifically, the invention provides targeted reagents that are detectable by imaging techniques and methods allowing the detection, localization and/or quantification of selectins in in vitro and ex vivo systems as well as in living subjects, including human patients. The methods provided are based on the use of selectin-targeted imaging agents comprising at least one fucoidan moiety having a high affinity and specificity for selectins, associated with at least one detectable moiety that allows visualization of the imaging agent using imaging techniques.

More specifically, the present invention provides methods for detecting the presence of selectins in a biological system comprising the step of contacting the biological system with an effective amount of a selectin-targeted imaging agent of the invention, or a pharmaceutical composition thereof. The contacting is preferably carried out under conditions that allow the imaging agent to interact with selectins present in the system so that the interaction results in the binding of the imaging agent to the selectins. The imaging agent that is bound to selectins present in the system is then detected using an imaging technique. One or more images of at least part of the biological system may be generated. The contacting may be carried out by any suitable method known in the art. For example, the contacting may be carried out by incubation.

The biological system may be any biological entity that can produce and/or contain selectins. For example, the biological system may be a cell, a biological fluid or a biological tissue. The biological system may originate from a living subject (e.g., it may be obtained by drawing blood, by biopsy or during surgery) or a deceased subject (e.g., it may be obtained at autopsy). The subject may be human or another mammal. In certain preferred embodiments, the biological system originates from a patient suspected of having a clinical condition associated with selectins.

The present invention also provides methods for detecting the presence of selectins in a patient. The methods comprise administering to the patient an effective amount of a selectin-targeted imaging agent of the invention, or a pharmaceutical composition thereof. The administration is preferably carried out under conditions that allow the imaging agent (1) to reach the area(s) of the patient's body that may contain abnormal selectins (i.e., selectins associated with a clinical condition) and (2) to interact with such selectins so that the interaction results in the binding of the imaging agent to the selectins. After administration of the selectin-targeted imaging agent and after sufficient time has elapsed for the interaction to take place, the imaging agent bound to abnormal selectins present in the patient is detected by an imaging technique. One or more (e.g., a series) images of at least part of the body of the patient may be generated. One skilled in the art will know, or will know how to determine, the most suitable moment in time to acquire images following administration of the imaging agent. Depending on the imaging technique used (e.g., MRI), one skilled in the art will also know, or know how to determine, the optimal image acquisition time (i.e., the period of time required to collect the image data).

The present Applicants have found that in contrast to what has been reported concerning targeted USPIOs (Hyafil et al., Arterioscl. Thromb. Vasc. Biol., 2006, 26: 176-181), the selectin-targeted USPIO-fucoidan nanoparticles according to the invention do no require an image acquisition time of several hours. Indeed, they were able to show that the USPIO-fucoidan nanoparticles required less than 30 minutes of MR image acquisition to depict with high sensitivity an intravenous thrombus in a rat model of vascular injury. Accordingly, in embodiments where USPIO-fucoidan nanoparticles according to the invention are used to detect the presence of selectins in a patient or to diagnose a pathological condition associated with selectins in a patient, the methods of the invention may further comprise a step of acquiring an MR image for 1 hour or less than 1 hour, e.g., for 50 minutes, 45 minutes, 40 minutes, 35 minutes, 30 minutes, 25 minutes, 20 minutes, 15 minutes, or less than 15 minutes. The MR image acquisition may start 30 minutes after administration the USPIO-fucoidan nanoparticles to patient or more than 30 minutes after such administration, e.g., 45 minutes, 60 minutes or 90 minutes.

Administration of the selectin-targeted imaging agent, or pharmaceutical composition thereof, can be carried out using any suitable method known in the art such as administration by oral and parenteral methods, including intravenous, intraarterial, intrathecal, intradermal and intracavitory administrations, and enteral methods.

As mentioned above, the imaging agent bound to selectins (present either in a biological system or in a patient) is detected using an imaging technique such as contrast-enhanced ultrasonography, planar scintigraphy, SPECT, MRI, fluorescence spectroscopy, or a combination thereof.

The methods of the invention that provide for detecting the presence of selectins in a patient or in a biological system obtained from a patient can be used to diagnose a pathological condition associated with selectins. The diagnosis can be achieved by examining and imaging parts of or the whole body of the patient or by examining and imaging a biological system (such as one or more samples of biological fluid or biological tissue) obtained from the patient. One or the other method, or a combination of both, will be selected depending of the clinical condition suspected to affect the patient. Comparison of the results obtained from the patient with data from studies of clinically healthy individuals will allow determination and confirmation of the diagnosis.

These methods can also be used to follow the progression of a pathological condition associated with selectins. For example, this can be achieved by repeating the method over a period of time in order to establish a time course for the presence, localization, distribution, and quantification of "abnormal" selectins in a patient.

These methods can also be used to monitor the response of a patient to a treatment for a pathological condition associated with selectins. For example, an image of part of the patient's body that contains "abnormal" selectins (or an image of part of a biological system originating from the patient and containing "abnormal" selectins) is generated before and after submitting the patient to a treatment. Comparison of the "before" and "after" images allows the response of the patient to that particular treatment to be monitored.

Pathological conditions that may be diagnosed, or whose progression can be followed using the inventive methods provided herein may be any disease and disorder known to be associated with selectins, i.e., any condition that is characterized by undesirable or abnormal interactions mediated by selectins. Examples of such conditions that may advantageously be diagnosed using methods provided herein include, but are not limited, thrombosis, myocardial ischemia/reperfusion injury, stroke and ischemic brain trauma, neurodegenerative disorders, tumor metastasis and tumor growth, and rheumatoid arthritis.

The present Applicants have shown that the selectin-targeted USPIO-fucoidan nanoparticles that they developed were able to detect intravascular thrombus as small as 100 µm. Consequently, the USPIO-fucoidan nanoparticles according to the invention may be used in the early detection of vulnerable plaques, in particular in at risk atherothrombotic patients. Risks factors of atherothrombotic disease include for example age, gender, family history, cigarette smoking history, hypertension, diabetes, cholesterol, obesity, and physical inactivity.

III—Pharmaceutical Compositions

In the methods of detection/imaging of selectins and of diagnosis of pathological conditions associated with selectins described herein, the imaging agents of the present invention may be used per se or as a pharmaceutical composition. Accordingly, in one aspect, the present invention provides for the use of fucoidan for the manufacture of a composition for the diagnosis of clinical conditions associated with selectins. In a related aspect, the present invention provides pharmaceutical compositions comprising at least one selectin-targeted imaging agent of the invention (or any physiologically tolerable salt thereof), and at least one pharmaceutically acceptable carrier.

The specific formulation will depend upon the selected route of administration. Depending on the particular type of pathological condition suspected to affect the patient and the body site to be examined, the imaging agent may be administered locally or systemically, delivered orally (as solids, solutions or suspensions) or by injection (for example, intravenously, intraarterially, intrathecally (i.e., via the spinal fluid), intradermally or intracavitory).

Often, pharmaceutical compositions will be administered by injection. For administration by injection, pharmaceutical compositions of imaging agents may be formulated as sterile aqueous or non-aqueous solutions or alternatively as sterile powders for the extemporaneous preparation of sterile injectable solutions. Such pharmaceutical compositions should be stable under the conditions of manufacture and storage, and must be preserved against the contaminating action of microorganisms such as bacteria and fungi.

Pharmaceutically acceptable carriers for administration by injection are solvents or dispersion media such as aqueous solutions (e.g., Hank's solution, alcoholic/aqueous solutions, or saline solutions), and non-aqueous carriers (e.g., propylene glycol, polyethylene glycol, vegetable oil and injectable organic esters such as ethyl oleate). Injectable pharmaceutical compositions may also contain parenteral vehicles (such as sodium chloride and Ringer's dextrose), and/or intravenous vehicles (such as fluid and nutrient replenishers); as well as other conventional, pharmaceutically acceptable, non-toxic excipients and additives including salts, buffers, and preservatives such as antibacterial and antifungal agents (e.g., parabens, chlorobutanol, phenol, sorbic acid, thimerosal, and the like). Prolonged absorption of the injectable compositions can be brought about by adding agents that can delay absorption (e.g., aluminum monostearate and gelatin). The pH and concentration of the various components can readily be determined by those skilled in the art.

Sterile injectable solutions are prepared by incorporating the active compound(s) and other ingredients in the required amount of an appropriate solvent, and then by sterilizing the resulting mixture, for example, by filtration or irradiation. The methods of manufacture of sterile powders for the preparation of sterile injectable solutions include vacuum drying and freeze-drying techniques.

In general, the dosage of a selectin-targeted imaging agent (or pharmaceutical composition thereof) will vary depending on considerations such as age, sex and weight of the patient, as well as the particular pathological condition suspected to affect the patient, the extent of the disease, the area(s) of the body to be examined, and the sensitivity of the detectable moiety. Factors such as contraindications, therapies, and other variables are also to be taken into account to adjust the dosage of imaging agent to be administered. This, however, can be readily achieved by a trained physician.

In general, a suitable daily dose of a selectin-targeted imaging agent (or pharmaceutical composition thereof) corresponds to the lowest amount of imaging agent (or pharmaceutical composition) that is sufficient to allow detection/imaging of any relevant (i.e., generally overexpressed) selectin present in the patient. To minimize this dose, it is preferred that administration be intravenous, intramuscular, intraperitoneal or subcutaneous, and preferably proximal to the site to be examined. For example, intravenous administration is appropriate for imaging the cardio/neurovascular system; while intraspinal administration is better suited for imaging of the brain and central nervous system.

IV—Kits

In another aspect, the present invention provides kits comprising materials useful for carrying out the diagnostic methods of the invention. The diagnostic procedures described herein may be performed by clinical laboratories, experimental laboratories, or practitioners.

In certain embodiments, an inventive kit comprises at least one fucoidan and at least one detectable entity, and, optionally, instructions for associating the fucoidan and detectable entity to form a selectin-targeted imaging agent according to the invention. The detectable entity is preferably a short-lived radionuclide such as technetium-99m ($^{99m}$Tc), gallium-67 ($^{67}$Ga), yttrium-91 ($^{91}$Y), indium-111 ($^{111}$In), rhenium-186 ($^{186}$Re), and thallium-201 ($^{201}$Tl). Preferably, the fucoidan and detectable entity are present, in the kit, in amounts that are sufficient to prepare a quantity of imaging agent that is suitable for the detection of selectins and diagnosis of a particular clinical condition in a subject.

In other embodiments, an inventive kit comprises at least one selectin-targeted imaging agent according to the invention. In such embodiments, the selectin-targeted imaging agent is preferably chemically stable.

A kit according to the present invention may further comprise one or more of: labeling buffer and/or reagent; purification buffer, reagent and/or means; injection medium and/or reagents. Protocols for using these buffers, reagents and means for performing different steps of the preparation procedure and/or administration may be included in the kit.

The different components included in an inventive kit may be supplied in a solid (e.g., lyophilized) or liquid form. The kits of the present invention may optionally comprise different containers (e.g., vial, ampoule, test tube, flask or bottle) for each individual component. Each component will generally be suitable as aliquoted in its respective container or provided in a concentrated form. Other containers suitable for conducting certain steps of the preparation methods may also be provided. The individual containers of the kit are preferably maintained in close confinement for commercial sale.

In certain embodiments, a kit further comprises instructions for using its components for the diagnosis of clinical conditions associated with selectins according to a method of the present invention. Instructions for using the kit according to a method of the invention may comprise instructions for preparing an imaging agent from the fucoidan and detectable moiety, instructions concerning dosage and mode of administration of the imaging agent, instructions for performing the detection of selectins, and/or instructions for interpreting the results obtained. A kit may also contain a notice in the form prescribed by a governmental agency regulating the manufacture, use or sale of pharmaceuticals or biological products.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results reported below were presented in scientific articles (L. Bachelet et al., Biochim. Biophys. Acta, 2009, 1790: 141-146; Rouzet et al., J. Nucl. Med., 2011, 52: 1433-1440), which are incorporated herein by reference in their entirety. Other results reported below were presented at the International Carbohydrate Symposium, Oslo, Norway, Jul. 24-Aug. 1, 2008 (L. Bachelet et al., "Fucoidan: A sulfated polysaccharide to target activated platelets in atherosclerosis").

Example 1

LMW Fucoidans are Highly Specific Ligands of P-Selectin

Materials and Methods

Chemical Products.

Fluorescein isothiocyanate (FITC) was purchased from Fluka (Saint-Quentin Fallavier, France); streptavidin-peroxidase conjugate from Dako (Trappes, France); diaminopropane, sodium cyanobromohydride and peroxidase substrate ABTS from Sigma-Aldrich (Saint-Quentin Fallavier, France); sinapinic acid solution from Bio-Rad Laboratories (Hercules, Calif., USA); and the amine coupling kit and running buffer from BIAcore (Uppsala, Sweden).

Polysaccharides.

The low molecular weight fucoidan (based on sulfated repeating fucose unit; M=7200 g/M; $SO_4$=30% (w/w)) was prepared from brown seaweed as previously described (A. Nardella et al., Carbohydr. Res., 1996, 289: 201-208). The low molecular weight heparin (M=5700 g/M; $SO_4$=45% (w/w)) and low molecular weight dextran sulfate (M=8000 g/M; $SO_4$=52% (w/w)), were supplied from Sigma-Aldrich; and the biotinylated polyacrylamide-type glycoconjugate containing 20% mol $SLe^X$ was obtained from Lectinity Holding (Moscow, Russia).

Biological Compounds.

Recombinant human P-selectin (121-124 kDa by SDS-PAGE) and recombinant human P-selectin/Fc chimera (146-160 kDa by SDS-PAGE) were obtained from R&D Systems (Lille, France); bovine serum albumin (BSA), thrombin receptor-activating peptide (TRAP), and adenosine diphosphate (ADP) from Sigma-Aldrich, and purified peptide and protein standards from Bio-Rad Laboratories.

Antibodies.

The PC5-labeled IgG (MOPC-21 clone), PC5-labeled antihuman P-selectin (CD62P, AK-4 clone), FITC-labeled IgM and FITC-labeled PAC-1 (directed to active conformation of integrin complex GPIIb/IIIa) were supplied from BD Biosciences (Le Pont de Claix, France); FITC-labeled IgG (MOPC-21 clone), FITC-labeled anti-human CD41 (integrin GPIIb) and goat anti-human Fc IgGperoxidase from Beckman-Coulter (Roissy, France); goat anti-human Fc IgG from Sigma-Aldrich; anti-human P-selectin (CD62P, G1 clone) from COGER (Paris, France).

Other Materials.

Immulon 1B microtiter plates were a gift from VWR (Fontenay sous Bois, France). Anionic protein chips CM10 were obtained from Bio-Rad Laboratories; CM5 sensor chips from BIAcore.

FITC Labeling of Polysaccharides.

Five hundred (500) mg of polysaccharide and 250 mg of $NaBH_3CN$ were added to 4 mL of diaminopropane hydrochloride solution at 2.5 M. After 24 hours at 60° C., 250 mg of $NaBH_3CN$ were added to the mixture and the reaction was carried on for 48 hours. Samples were dialyzed (cut-off 1000 Da) before freezedrying. One hundred and fifty (150) mg of aminated polysaccharide was dissolved in 6 mL of 0.5 M carbonate buffer (pH 9.6). Six (6) mg of FITC was added to the solution which was stirred at 4° C. in darkness for 2 hours. After neutralization, the solution was dialyzed (cut-off 1000 Da) and freeze-dried. The colored compound was then dissolved at 150 mg/mL in NaCl 1 M, precipitated by ethanol and centrifuged at 4500 rpm for 20 minutes to remove the free fluorescein. Fucoidan was successfully fluorolabeled using this protocol with a grafting of 0.19±0.06 fluorophore per polysaccharide chain.

P-Selectin Binding Assay with Sialyl Lewis X.

This protocol was adapted from a previously described method (Weitz-Schmidt et al., Anal. Biochem., 1999, 273: 81-88). P-selectin/Fc chimera (5 µg/mL in phosphate buffered saline, PBS, 137 mM NaCl, 8.1 mM $Na_2HPO_4$, 1.4 mM $KH_2PO_4$ and 2.7 mM KCl, pH=7.2) was coated onto microtiter plates overnight at 4° C. The plates were washed with the assay buffer (20 mM Hepes, pH 7.4, containing 150 mM NaCl and 1 mM $CaCl_2$), blocked for 4 hours at 4° C. with 3% BSA in the same buffer, and washed again. Polysaccharides or anti-human P-selectin (G1 clone) and biotinylated $SLe^X$-polymer were diluted in the assay buffer and added to the P-selectin-coated wells or the BSA-coated wells (non specific control) for incubation overnight at 4° C. The plates were then washed and streptavidin-peroxidase diluted 1:1000 in the assay buffer was added to the wells. After 4 hours at 4° C., the plates were washed with assay buffer. ABTS peroxidase substrate solution was added and the color reaction was stopped after 10 minutes with 2% oxalic acid. Bound $SLe^X$-polymer was determined by measuring the optical density at 405 nm using a microplate reader.

P-Selectin Binding Assay with PSGL-1.

P-selectin (5 µg/mL in PBS, 137 mM NaCl, 8.1 mM $Na_2HPO_4$, 1.4 mM $KH_2PO_4$ and 2.7 mM KCl, pH=7.2) was coated onto microtiter plates overnight at 4° C. The plates were washed with the assay buffer (20 mM Hepes, pH 7.4, containing 150 mM NaCl and 1 mM $CaCl_2$), blocked for 4 hours at 4° C. with 3% BSA in the same buffer, and washed again. Fucoidan and PSGL-1/Fc chimera were diluted in the assay buffer and added to the P-selectin-coated wells or the BSA-coated wells (non specific control) for incubation overnight at 4° C. The plates were then washed and IgG antiFc-peroxidase diluted 1:1000 in the assay buffer was added to the wells. After 4 hours at 4° C., the plates were washed with the assay buffer. ABTS peroxidase substrate solution was added and the color reaction was stopped after 5 minutes with 2% oxalic acid. Bound PSGL-1 was determined by measuring the optical density at 405 nm using a microplate reader.

SELDI-TOF Analysis.

Anionic protein chip arrays CM10 were employed. Spots were prewetted twice for 5 minutes with 5 µL of Hepes pH 7.0. Samples were prepared by mixing 500 ng of recombinant human P-selectin in the absence or in the presence of different concentrations of polysaccharides (molar ratio between P-selectin and polysaccharide of 1 per 1 to 1 per 100), diluted in 1 M Hepes pH 7.0, in a total volume of 5 µL, and incubated for 1 hour at 4° C. The samples were applied to the spots and incubated for 45 minutes at room temperature in a humid chamber. The spots were washed three times with 5 µL of 1 M Hepes pH 7.0 and twice with 5 µL of distilled water and then air-dried for 10 minutes. One (1) µL of a saturated solution of sinapinic acid (in 50% acetonitrile, 0.5% trifluoroacetic acid) was applied twice to each spot. The protein chip arrays were analyzed using a protein chip reader (PBS II, Bio-Rad). The protein masses were calibrated externally using purified peptide and protein standards. Spectra were analyzed with protein chip software 3.1.1 (Bio-Rad).

Surface Plasmon Resonance.

BIAcore 2000 optical biosensor was used. The carboxymethylated dextran surface CM5 sensor chip was coupled with goat anti-human Fc IgG using standard amine coupling chemistry (averaged 6500 RU). Recombinant human P-selectin/Fc chimera was then captured to the chip (averaged 1750 RU). Goat anti-human Fc IgG was used as non specific control. Samples were diluted in running buffer (10 mM Hepes, 150 mM NaCl, 1 mM $CaCl_2$, and 0.005% Tween-20, pH 7.4). Flow cell, temperature, flowrate, sample volume, and mixing were selected using the BIAcore control software. Sensorgrams were analyzed using the BIA evaluation software.

Flow Cytometry.

Blood from healthy adult donors was collected into sodium citrate 3.8% (w/v). Citrated human whole blood (5 µL) was diluted to 40 µL with PBS (137 mM NaCl, 8.1 mM $Na_2HPO_4$, 1.4 mM $KH_2PO_4$ and 2.7 mM KCl, pH=7.2). Platelets were activated by adding ADP at a final concentration of 2.5 µM or TRAP at a final concentration of 200 µM. Five µL of LMW polysaccharides (FITC-labeled or not, diluted in PBS) and 5 µL of fluorolabeled antibody (PC5-labeled antiCD62P AK-4 clone or FITC-labeled PAC-1 or FITC-labeled antiCD41; diluted 8:100; 5:100 and 3:100 in PBS) were added at room temperature for 20 minutes. The solutions were diluted to 1 mL with PBS before analysis by flow cytometry. Data were collected on a Coulter EPICS XL-MCL flow cytometer (Beckman Coulter). Samples analysis was performed on side and forward scatter, and fluorescence was acquired in FL1 (fluorescein) or FL4 (PC5) using the logarithmic mode. 7500 events were collected from each sample. The level of platelet activation was assessed by the positivity of the anti-Pselectin (CD62P, AK-4 clone) antibody (0.4%, 73.4%, and 97.8% for non-activated, ADP-activated and TRAP-activated platelets, respectively). Data were processed using GEN S® System II software (Beckman Coulter) and histograms are presented overlapped for the different conditions.

Statistical Analysis.

Data shown are representative results of at least three identical and independent experiments carried out each time with n≥3 samples per conditions. Statistical comparisons were performed with the Student's t-test.

Results

LMW fucoidan inhibits the binding of $SLe^X$ and PSGL-1 to P-selectin.

Figure 1:
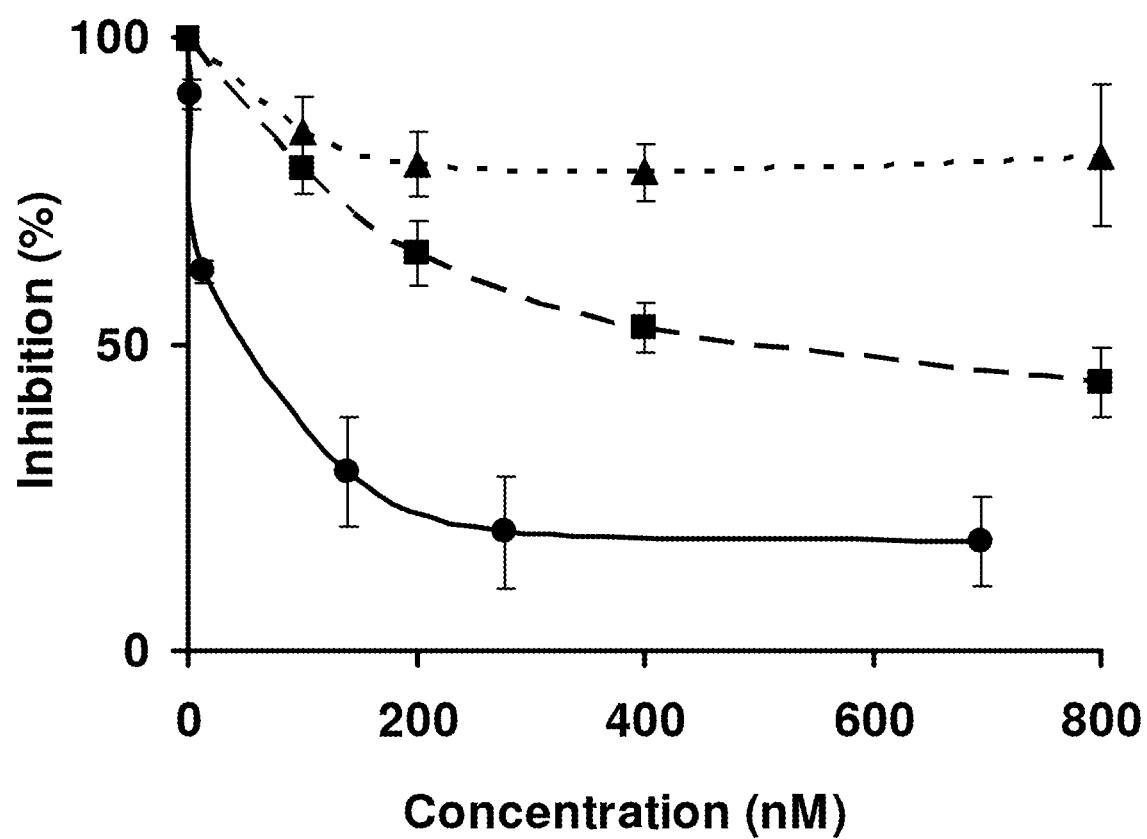
FIG. 1 is a graph showing inhibition of SLe$^x$/P-selectin binding by sulfated polysaccharides. Binding of SLe$^x$ polyacrylamide-biotin to P-selectin immobilized onto a microtiter plate was quantified by streptavidin-peroxidase complexation and peroxidase reaction recorded at 405 nm in the presence of increasing concentrations of dextran sulfate (▲), heparin (■) and fucoidan (●), as described in Example 1. The results of a representative experiment are shown [mean±SD (n≥3)].

The binding of $SLe^X$-polyacrylamide-biotin to immobilized P-selectin was measured in the presence of LMW fucoidan, heparin and dextran sulfate. In this assay, an anti-human P-selectin antibody (clone G1, as a positive control) completely blocked the binding of $SLe^X$ to P-selectin. The amount of $SLe^X$ bound to P-selectin decreased with increasing concentrations of polysaccharides. However, major differences were observed between the sulfated polysaccharides (FIG. 1). Inhibition by fucoidan was much more pronounced than with heparin and dextran sulfate, with an $IC_{50}$ of 20 nM, 400 nM and >25,000 nM, respectively. The binding of PSGL-1/Fc chimera to immobilized P-selectin was also evaluated in the presence of LMW fucoidan. The amount of PSGL-1 bound to P-selectin decreased with increasing concentration of fucoidan with an $IC_{50}$ of 5 nM.

Binding of LMW fucoidan to P-selectin.

The binding of P-selectin was then analyzed by mass spectrometry and by surface plasmon resonance (SPR). The formation of a complex between P-selectin and the three LMW sulfated polysaccharides and native dextran was analyzed using SELDI-TOF MS. Anionic chips on which P-selectin bound (isoelectric point ~6.5) at physiological pH=7 were used. P-selectin was then desorbed by laser and detected as a SELDI-TOF broad peal of ~100 kDa. The amount of P-selectin markedly decreased the presence of LMW fucoidan, and in a dose-dependent manner. P-selectin retention to the chip also decreased with heparin but was not affected by incubation with native dextran or dextran sulfate. These results demonstrate that LMW fucoidan forms a complex with P-selectin in solution thus preventing its retention to the anionic surface.

Figure 2:
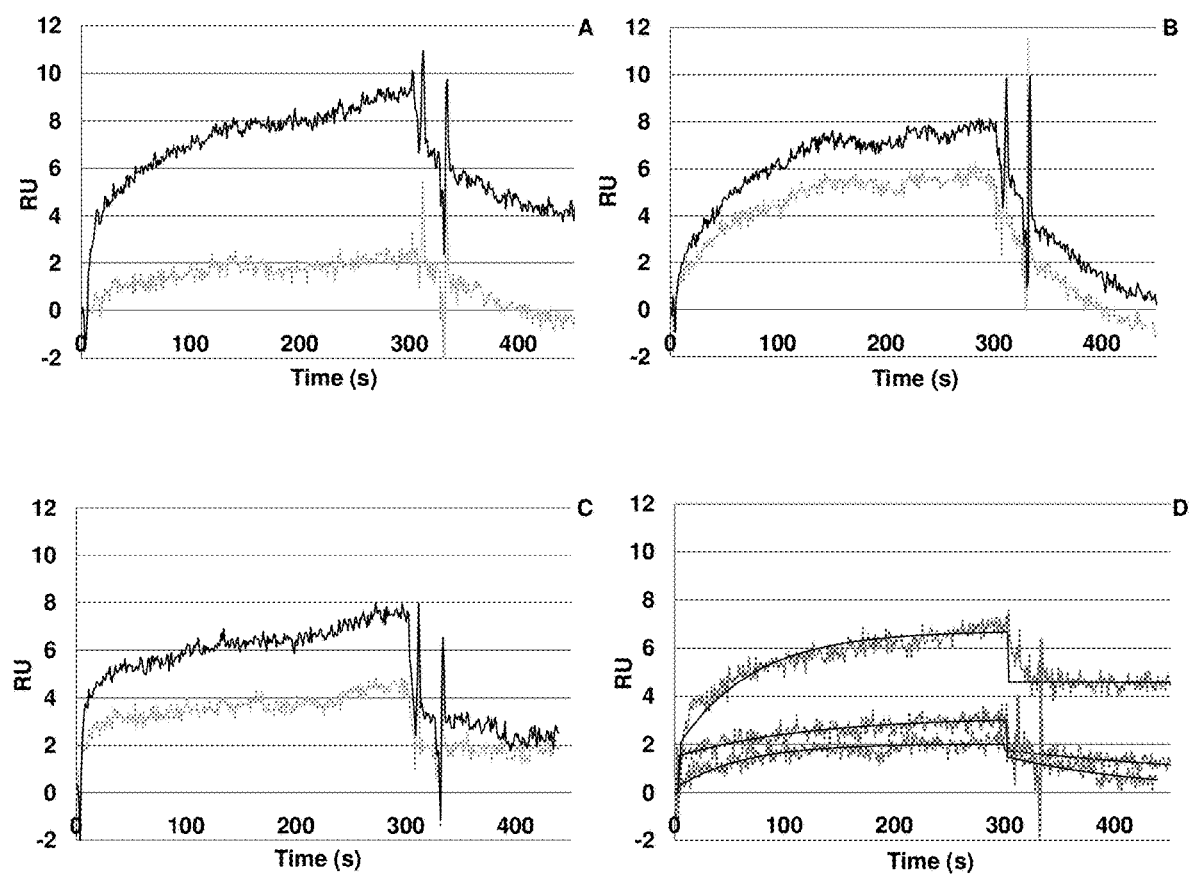
FIG. 2 is a set of representative sensorgrams showing the association and dissociation profiles of sulfated polysaccharides on immobilized IgG or P-selectin. Fucoidan (A), heparin (B) and dextran sulfate (C) were injected over SPR CM5 sensorchips on which were immobilized goat anti-human Fc IgG (grey recording, non specific control) plus P-selectin/Fc chimera (black recording). Kinetic studies were performed at a flow rate of 30 μL/min. Representative sensorgrams in resonance units (RU) are overlaid at a similar 1 μM concentration for all LMW sulfated polysaccharides. Dissociation constants were calculated using a 1:1 Langmuir binding model plot (D) for the specific binding of P-selectin with fucoidan (upper curve), heparin (lower curve) or dextran sulfate (middle curve). Non-specific binding on IgG was observed for each of the polysaccharides.

The binding characteristics of LMW sulfated polysaccharides to P-selectin were further compared using surface plasmon resonance analysis. LMW fucoidan, heparin and dextran sulfate were flowed on a sensorchip coated either with anti-human Fc IgG or with recombinant human P-selectin/Fc chimera (FIG. 2). All polysaccharides bound to P-selectin and, to a lesser extent, to anti-human Fc IgG used as a control. The signal difference obtained on P-selectin vs IgG was higher with fucoidan than with heparin or dextran sulfate, which suggests that fucoidan exhibits a better selectivity (FIG. 2A). Dissociation constants of LMW fucoidan, heparin and dextran sulfate for P-selectin, calculated using a 1:1 Langmuir binding model (FIG. 2D), were found to be 1.2 nM, 577 nM and 118 nM, respectively. These results confirmed that LMW fucoidan has an affinity for P-selectin at least two orders of magnitude higher than the two other polysaccharides.

Binding of LMW Fucoidan to Human Platelets.

Figure 3:
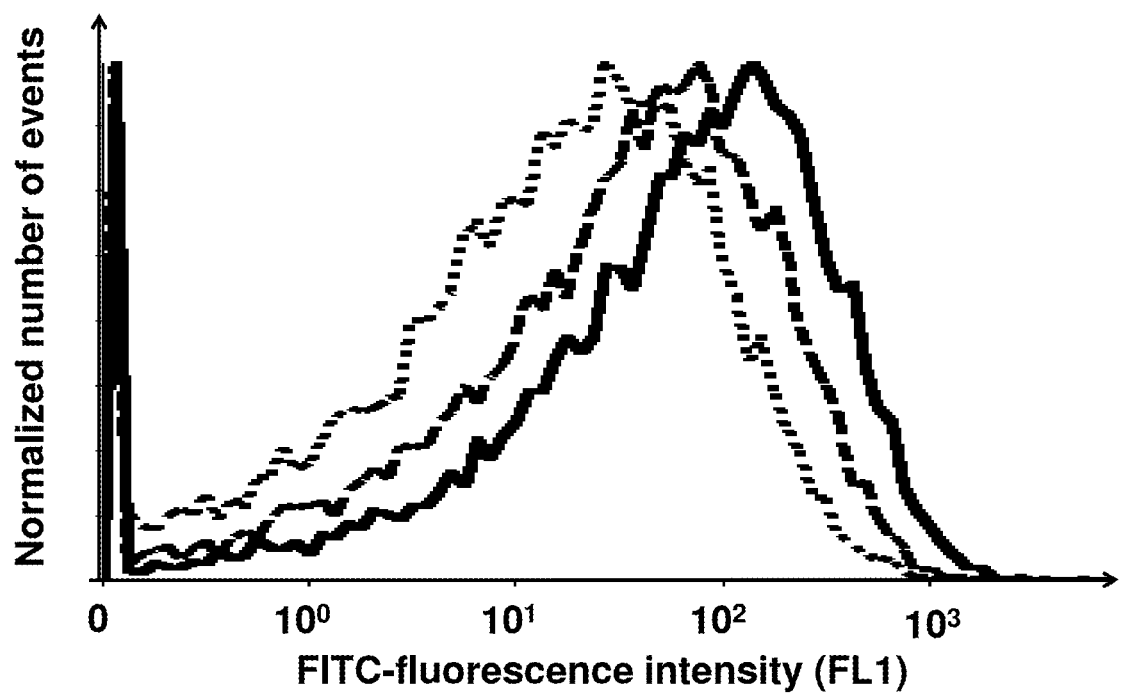
FIG. 3 is a graph showing the binding of FITC-coupled LMW fucoidan to human platelets in whole blood. FITC-coupled LMW fucoidan at 140 μM (1 mg/mL) was incubated for 20 minutes at room temperature with citrated human blood diluted 10 times in PBS. Activation of platelets was induced with 2.5 μM ADP (medium activator; dotted line) or 200 μM TRAP (strong activator; full line). Platelets were identified by their side and forward scatter and their positivity for a fluorolabeled specific platelet antibody in flow cytometry. Binding of FITC-coupled LMW fucoidan to platelets was detected on the FL1 channel. Similar results were obtained using two other donors.

Heparin was previously reported to bind to platelets (J. Hirsh et al., Chest, 2004, 126: 188S-203S; R. Verhaege, Acta Cardiol., 1998, 53: 15-21). Flow cytometry experiments were performed by incubating human citrated whole blood with FITC-labeled LMW fucoidan. A representative experiment is reported on FIG. 3. Platelets were gated on side and forward scatter and their positivity for a fluorolabeled specific platelet antibody (CD41). FITC-labeled fucoidan bound to activated platelets as demonstrated by a shift of the fluorescence to the right. Fucoidan binding increased with the level of platelet activation as indicated by the percentage of positive platelets, 34.7%, 51.4%, and 69.1% for nonactivated, ADP-activated and TRAP-activated platelets, respectively.

Figure 4:
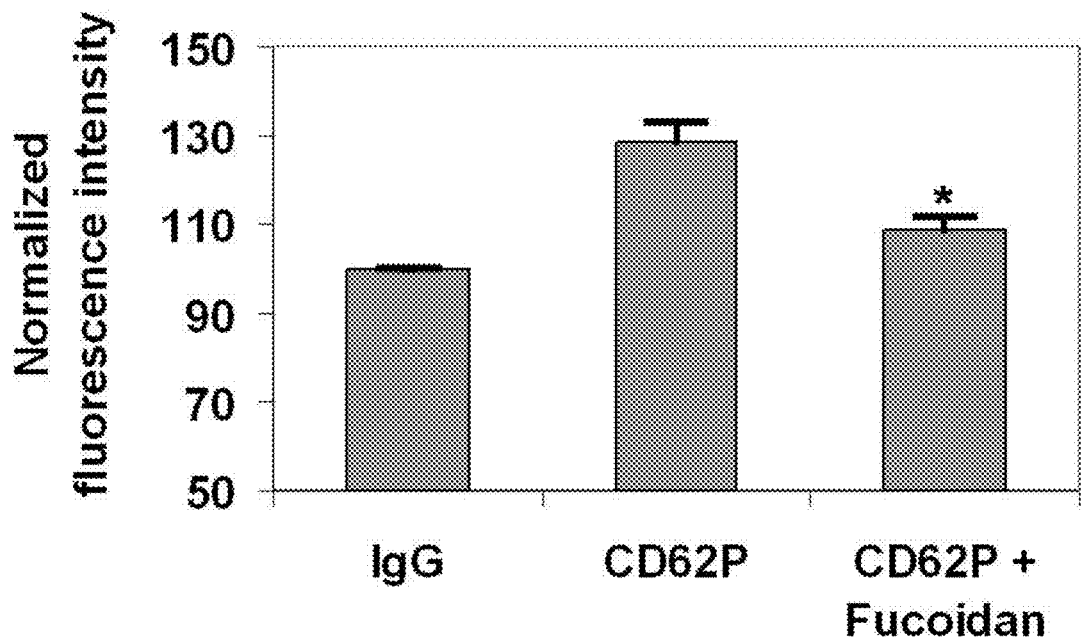
FIG. 4 is a graph showing the binding inhibition of labeled CD62P antibody to platelets in the presence of LMW fucoidan. CD62P antibody was incubated in the presence or in the absence of non-labeled LMW fucoidan, as described in Example 1. Activation of platelets was induced by 200 μM TRAP. Platelets were identified by their side and forward scatter and their positivity for a fluorolabeled specific platelet antibody in flow cytometry. Binding to activated platelets of non-relevant PC5-labeled IgG antibody is reported for comparison. The binding of PC5-labeled CD62P antibody to platelets, observed on the FL4 channel, significantly decreased in the presence of LMW fucoidan. Values of mean fluorescence intensity (MFI) were normalized to the value obtained by incubation with non-relevant IgG alone. *p<0.05 between data with CD62P alone with Student's t-test.

TRAP-activated platelets were then incubated with a fluorolabeled anti-CD62P antibody in whole blood in the presence or in the absence of non-fluorolabeled LMW fucoidan. Inhibition of the CD62P antibody binding to activated platelets was observed in the presence of LMW fucoidan as indicated by a decrease in the mean fluorescence intensity (FIG. 4). In addition, LMW fucoidan did not inhibit the binding of CD41 (integrin GPIIb) antibody or PAC-1 (directed to the active conformation of the integrin complex GPIIb/IIIa) to activated platelets, indicating that its effect on CD62P antibody binding to activated platelets was specific. Taken together, these results indicate that the binding of LMW fucoidan to activated platelets observed in whole human blood was mediated by P-selectin.

Discussion

Sulfated carbohydrates are known to have a wide variety of biological activities (S. Soeda et al., Biochim. Biophys. Acta, 2000, 1497: 127-137). Sulfated polysaccharides have previously been described as P-selectin ligands (A. Varki et al., PNAS, 1994, 91: 7390-7397; D. Simonis et al., Biochemistry, 2007, 46: 6156-6164) e.g., heparin and modified heparins (A. Koenig et al., J. Clin. Invest., 1998, 101: 877-889), high molecular weight fucoidan and dextran sulphate (M. P. Skinner et al., J. Biol. Chem., 1991, 266: 5371-5374). In the present study, the interaction of three low molecular weight sulfated polysaccharides (fucoidan, heparin and dextran sulfate) with P-selectin was characterized using four different methods. LMW fucoidan is a promising candidate for the treatment of inflammation disorders (K.

Senni et al., Arch. Biochem. Biophys., 2006, 445: 56-64) and cardiovascular diseases (33; 34; F. Zemani et al., Arterioscler. Thromb. Vasc. Biol., 2008, 28: 644-650). LMW heparin is used in the treatment of thrombotic disorders (K. A. Fox et al., Eur. Heart J., 2000, 21: 1440-1449). Synthetic dextran sulfate and mimetics were also investigated as putative drugs in various diseases, including infection diseases (J. Neyts et al., Biochem. Pharmacol., 1995, 50: 743-751).

The inhibition of SLe$^x$/P-selectin binding was quantified in binding assay experiments ranking polysaccharides as follows ($IC_{50}$): fucoidan (20 nM)>heparin (400 nM)>dextran sulfate (25,000 nM). As a comparison, Koenig et al. established by inhibition assays that heparin inhibited P-selectin binding to Sialyl Lewis X with $IC_{50}$ between 82 and 2400 µM depending on the size of the heparin fragment (A. Koenig et al., J. Clin. Invest., 1998, 101: 877-889). However, in their work, Sialyl Lewis X was immobilized whereas, in the present approach, it is P-selectin that was immobilized. The functional importance of LMW fucoidan binding to P-selectin was evidenced by the interference in the interaction between the glycoprotein with its natural ligand PSGL-1.

SELDI-TOF mass spectrometry was used to highlight the formation of a complex between P-selectin and LMW polysaccharides. This tool has allowed to demonstrate the binding of heparin and fucoidan to thrombin and protease nexin-I (B. Richard et al., Thromb. Haemost., 2006, 95: 229-235). SELDI-TOF MS experiments showed that, in solution, LMW fucoidan formed a complex with P-selectin at physiological pH in a dose-dependent manner. The complex formation decreased P-selectin retention to an anionic surface.

The interaction of sulfated polysaccharides such as heparin or fucoidan with various proteins has been previously studied by surface plasmon resonance (BIAcore®) (32; H. Yu et al., Biochim. Biophys. Acta, 2005, 1726: 168-176). For instance, it was shown that a SLe$^x$ mimetic binds to P-selectin with $K_D$ of 114 µM (M. E. Beauharnois et al., Biochemistry, 2005, 44: 9507-9519) and PSGL-1 binds to P-selectin with $K_D$ of 320 nM (P. Mehta et al., J. Biol. Chem., 1998, 273: 32506-32513). The dissociation constant of LMW heparin for P-selectin calculated here, with a $K_D$ above 500 nM, is in the same range as those of three unfractioned heparins determined by quartz crystal microbalance measurements in the study of Simonis et al. (Biochemistry, 2007, 46: 6156-6164). Interestingly, this results demonstrated that LMW fucoidan with a $K_D$ in the nanomolar range is the most effective and selective P-selectin ligand when compared with other LMW polysaccharides, PSGL-1 and the SLe$^x$ mimetic. Moreover, P-selectin/LMW fucoidan interaction is stronger than the L-selectin/GlyCAM-1 interaction, also involved in leukocyte rolling on blood vessels endothelium. The interaction constant of this interaction was determined to be 108 µM by Nicholson et al. (J. Biol. Chem., 1998, 273: 763-770).

Native and fractionated heparins were shown to interact with P-selectin on HL-60 cells (Y. Gao et al., Mol. Cells, 2005, 19: 350-355). In order to determine whether the binding of fucoidan to P-selectin observed using purified proteins could occur in more complex conditions, the interaction of LMW polysaccharides with human platelets on whole blood was analyzed. Using flow cytometry, LMW fucoidan was found to bind to activated platelets and the level of binding was found to correlate with the degree of platelet activation. Moreover, LMW fucoidan was able to inhibit the binding of an anti P-selectin antibody to activated human platelets.

Example 2

$^{99m}$Tc-Labelled Fucoidan as P-Selectin-Targeted Imaging Agent for the In Vivo Scintigraphic Detection of Platelet Activation and Accumulation Fucoidan was labelled with technetium-99m ($^{99m}$Tc) using the well-known stannous reaction in solution. Briefly, 4 µL of stannous chloride were added to 10 µL of fucoidan (1 mg/mL, MW=7200) followed by 2 µL of potassium borohydride. Immediately after combination of these reagents, 50 µL of $^{99m}$Tc (corresponding to 15-30 mCi) were gently added to the mixture. The labelling reaction was complete after 1 hour of incubation. Control of the labelling was performed using thin layer paper chromatography and methyl-ketone as eluant. The percentage of labelling was 100%.

Figure 5:
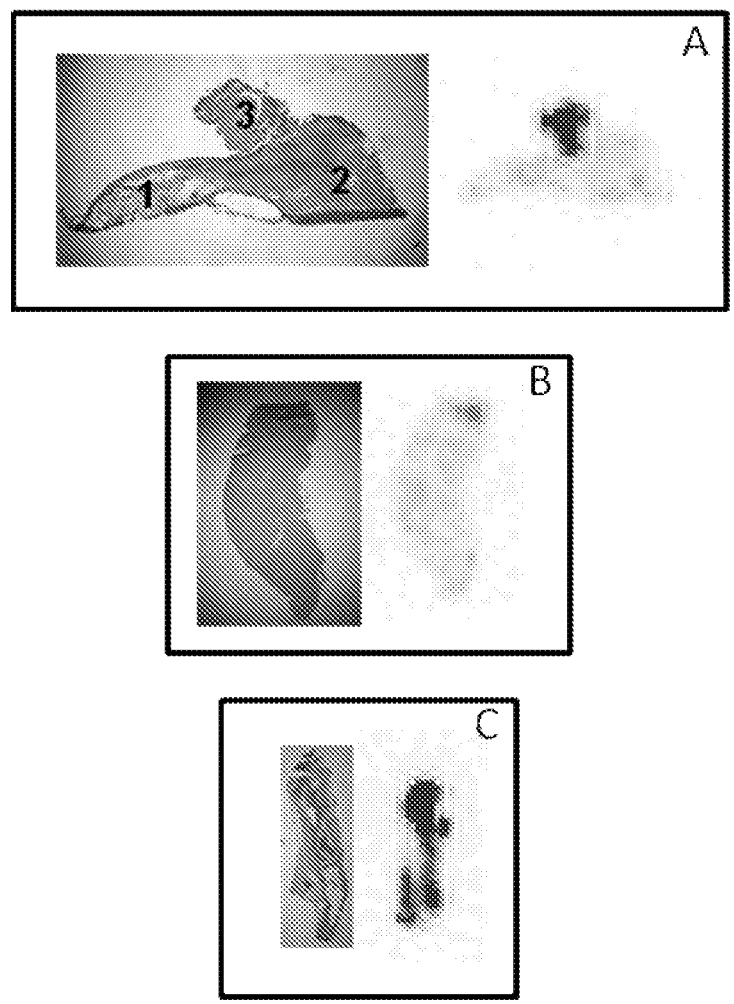
FIG. 5 shows histology (left) and autoradiography (right) sections of hearts in rat model of left endocarditis with aortic valve vegetations. (A) One histologic section vegetation is restricted to the valve (3) whereas the aorta (1) and the sub-valvular myocardium (2) were normal. On the autoradiography, the signal from $^{99m}$Tc-labelled fucoidan, injected in vivo, is exactly co-localized with the valvular vegetation. (B) A negative control of a myocardium without vegetation gives the background in autoradiography. (C) On the autoradiography, the signal from $^{99m}$Tc-labelled fucoidan is exactly co-localized with the fibrinoid cuff surrounding the catheter.
Figure 6:
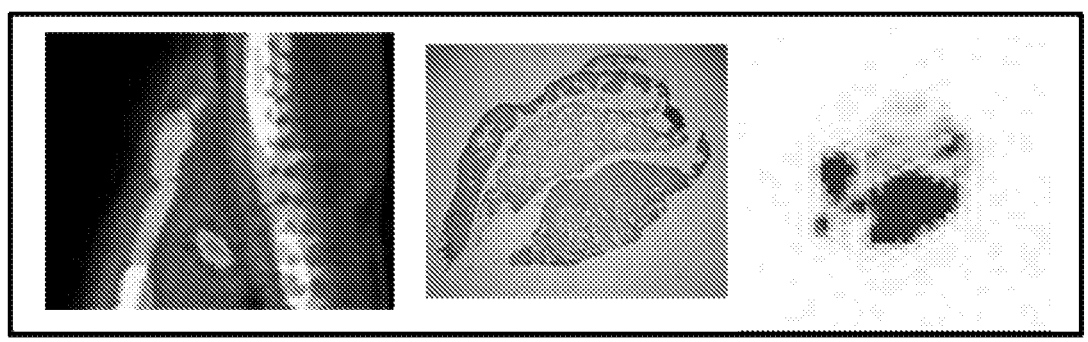
FIG. 6 shows tomography-SPECT in vivo imaging (left), histology (middle) and autoradiography (right) section in rat model of atrial thrombus. The tomography-SPECT shows retention of $^{99m}$Tc-labelled fucoidan in the rat left atrium. The histology results show that there is fibrinous thrombus in the atrial lumen with muscle on both sides. On the autoradiography, the signal from $^{99m}$Tc-labelled fucoidan is localized in the myocardium facing the thrombus.
Figure 7:
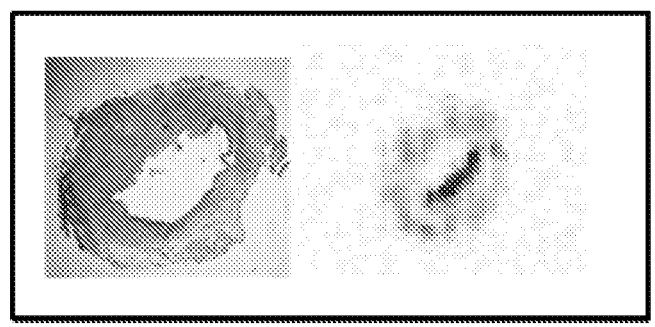
FIG. 7 shows histology (left) and autoradiography (right) sections of an abdominal aortic aneurysm in a rat model of aneurismal thrombus. On the autoradiography, the signal from $^{99m}$Tc-labelled fucoidan is localized at the lumen/vessel wall interface where a thin thrombus is localized on the histology picture.

Rat models of endocarditic vegetations, aneurysmal and atrial trombi were used as animal models of clinical conditions associated with platelet activation and fibrin formation. Intravenous injection of 1 µg of $^{99m}$Tc-labelled fucoidan allowed the in vivo visualization of platelet-rich endocarditic vegetations (FIG. 5), atrial (FIG. 6) and aneurysmal thrombi (FIG. 7). These in vivo data were confirmed by ex vivo autoradiography showing the exact histological co-localization of the signal with valves vegetations or thrombus with a very high quantitative signal to background ratio of 8 to 10.

The development of fucoidan as a radiotracer for selectin imaging can be considered at several steps: (1) ability to visualize P-selectin overexpression by acutely-activated endothelium (ischemia-reperfusion model); (2) ability to visualize E-selectin overexpression by chronically-stimulated endothelium (L-NAME model of hypertension); and (3) ability or not to visualize L-selectin accumulation in tertiary lymph node formation (aortic allograft in rats) and in autoimmune myocarditis.

Example 3

Preparation of Fucoidan-Coated USPIO Particles

The present Applicants have developed five different strategies to coat fucoidan onto USPIO particles.

The first strategy involves the synthesis of iron particles in the presence of unmodified fucoidan. The Applicants have applied a method of synthesis previously described with dextran (R. S. Molday et al., J. Immunol. Methods, 1982, 52: 353-367) replacing dextran MW 40000 by fucoidan MW 50500. Fucoidan-coated iron nanoparticles were obtained. However, these particles were found to be unstable in water.

The second strategy comprises the coating of an acidic ferrofluid with unmodified fucoidan. Fucoidan was incubated with acidic ferrofluid. Fucoidan-coated iron nanoparticles were obtained that were stable in aqueous medium pH 7.4, but unstable in buffers with ionic strength of 0.15 M, which are used in most applications. The synthesis could be obtained in the presence of a cross-linker (A. San Juan et al., J. Biomed. Mater Res. A, 2007, 82: 354-362) to increase the stability of the nanoparticles.

Three other strategies have been developed that are based on the grafting of fucoidan to maghemite γFe$_2$O$_3$ nanoparticles via a linker (strategy 3), or the coupling of fucoidan to dextan-coated maghemite γFe$_2$O$_3$ nanoparticles, i.e., coated with carboxymethyl dextran or CMD (strategy 4) or coated with oxidised dextran (strategy 5). In all these strategies, the first step is to functionalize the reducing end of fucoidan with a primary amine to allow subsequent reaction without altering the fucoidan chain structure and therefore its affinity for P-selectin.

In strategy 3, the iron nanoparticles were thiolated with dimercaptosuccinic acid (DMSA) as previously described (French patent No. 2 736 197; N. Fauconnier et al., J. Colloid Interface Sci., 1997, 194: 427-433), and then linked to the aminated fucoidan by a disulfide bridge using a heterobifunctional linker, N-succinimidyl 3-(2-pyridyldithio) propionate (SPDP) (J. Roger et al., Eur. Phys. J. Applied Phys., 1999, 5: 321-325). Iron nanoparticles coated with a LMW fucoidan (MW=7200) were obtained that were found to be stable in usual aqueous buffer pH 7.4 with ionic strength of 0.15 M.

In strategy 4, CMD (MW=15000) was incubated with acidic ferrofluid to obtain CMD-coated iron nanoparticles stable in usual aqueous buffer pH 7.4 with ionic strength of 0.15 M. Aminated fucoidan is grafted on these nanoparticles using standard amine coupling chemistry (with EDC/NHS system).

In strategy 5, aminated fucoidan is grafted to oxidized dextran-coated nanoparticles by formation of Schiff bases.

Example 4

Fucoidan-Coated Acoustically Active Microbubbles and Liposomes

Several strategies are investigated to graft fucoidan on ultrasound-based imaging contrast agents. In a first approach, aminated fucoidan is grafted to phospholipids-based, perfluorobutane-filled microbubbles using standard amine coupling chemistry as previously described by Villanueva et al. (Circulation, 1998, 98: 1-5). Briefly, perfluorobutane was dispersed by sonication in aqueous medium containing phosphatidylcholine, a surfactant, a phosphatidylethanolamine derivative and a phospholipid derivative containing carboxyl groups which were activated with 1-ethyl-3(3-dimethylaminopropyl) carbodiimide (EDC) and aminated fucoidan was then covalently attached via primary amino groups with the formation of amine bonds.

A second strategy is to graft biotinylated fucoidan to phospholipid-based, perfluorobutane-filled microbubbles via a multi-step avidin/biotin bridging chemistry as previously described by Weller et al. (Biotechnol. Bioeng., 2005, 92: 780-788). Briefly, an aqueous saline solution containing phosphatidylcholine, polyethylene glycol stearate and a biotinylated derivative of phosphatidylethanolamine was sonicated with perfluorobutane. The microbubbles formed were incubated with streptavidin, and then a saturating amount of biotinylated fucoidan.

Biotinylated fucoidan was obtained using a method previously described by Osmond et al. (Anal. Biochem., 202, 310(2), 199-207) for the biotinylation of an aminated heparin. Briefly, sulfosuccinimidyl-6-(biotinamido)hexanoate-(sulfo-NHS-LC-biotin) was added to a solution of aminated fucoidan in carbonate buffer 0.1 M pH=8 with a molar ratio between aminated fucoidan and sulfo-NHS-LC-biotin of 1 to 10. The mixture was vortexed and shaken overnight at 4° C., and was then dialyzed (cut-off 1000 Da) against bi-distilled water before freeze-drying.

Finally, a third approach is to graft fucoidan to acoustically active liposomes using a thiol chemistry as previously described by Hamilton et al. (Circulation, 2002, 105: 2772-2778). Briefly, component phospholipids (phosphatidylcholine, phosphatidyl-glycerol, phosphatidylethanolamine derivative and cholesterol) were dissolved in chloroform and mixed and the resulting film was sonicated in water to form liposomes; aminated fucoidan was reacted with 3-(2-pyridylthio)propionic acid-N-hydroxysuccinimide ester (SPDP). The fucoidan derivative was then reduced in dithiothreitol solution and the thiolated fucoidan was then conjugated to liposomes.

Example 5

Fucoidan Substituted with Iodinated Tyrosine for X-Ray Radiography

Another possibility for the radiolabelling of fucoidan is the use of sodium iodide after grafting of a tyrosine residue onto the reductive end of the polysaccharide. The substitution step is similar to the amination step described in Example 1.

Briefly, 200 mg of polysaccharide and 100 mg of NaBH$_3$CN were added to 1.6 mL of a tyrosine hydrochloride solution at 2.5 M. After 24 hours at 60° C., 100 mg of NaBH$_3$CN were added to the mixture and the reaction was prolonged for 48 hours. The sample was dialyzed (cut-off 1000 Da) against bidistilled water before freeze-drying. Modified fucoidan was recovered in a 50-70% yield with a grafting of 0.50±0.05 of tyrosine per polysaccharide chain.

Iodination was performed using chloramine-T as follows: 20 μmoles of modified fucoidan (14.5 mg) in 450 μL of phosphate buffer saline 0.05 M, pH 7.4 (PBS) were added to a NaI solution (150 μL of 8% w/v solution in PBS) followed by the addition of 350 μL of a chloramine-T solution (40 mg/mL in PBS). The mixture was vortexed, and shaken overnight at 4° C. The reaction mixture was then dialyzed against bidistilled water (cut off 1000 Da) and freeze-dried to get the iodinated modified fucoidan in quantitative yield.

Example 6

In Vivo P-Selectin Targeted Molecular Imaging of IntraLuminal Thrombus by MRI Using USPIO-Fucoidan in Experimental Abdominal Aoartic Aneurysms The Applicants have developed a novel approach to P-selectin molecular imaging using fucoidan, as pharmacophore, conjugated to neutral polysaccharide-enrobed nanoparticles of iron oxide (i.e., ultra small superparamagnetic iron-oxides, USPIOs), as contrastophore. The ability of this new contrast agent to detect active intravascular thrombus following elastase vascular injury was evaluated in vivo in an experimental model in rats (Anidjar et al., Circulation, 1990, 82: 973-981).

Materials and Methods

Contrast Agents.

USPIO coated with carbodymethyldextran (USPIO-CMD) and USPIO coated with fucoidan (USPIO-FUCO) were prepared as described below. The depolymerized fucoidan used, which was obtained from Algues et Mer (Ouessant, France), had a molecular weight of 7200 g/mol. After refinement of USPIO-FUCO and USPIO-CMD, the iron concentration of each contrast agent was adjusted to 25 mM.

Coating of Acidic Ferrofluide with CMD-Fucoidan.

The starting ferrofluide was synthesized using a classical method (Rivière et al., Radiology, 2005, 235: 959-967), and kept in acid ([Fe]=1.05 M). In a first step, the coating of acidic carboxymethyldextran (CMD, M=15000 g/mol, [COOH]=1.3 mmol/g, Sigma Aldrich) was performed according to the method described by Roger et al. (Eur. Phys. J. Applied Phys., 1999, 5: 321-325). A sample of 5 mL of USPIO-CMD ([Fe]=0.05 M) was treated with 20 mg of EDC and 3.0 mg of NHS for 15 minutes at room temperature. Fucoidan, which had previously been aminated at its reducing end using diaminopropane (Kondo et al., Agric. Biol. Chem., 1990, 54: 2169-2170; Seo et al., Bioconjug. Chem., 2007, 18: 2197-2201), was added to the reaction mixture ([fucoidan]=15 mg/ml) and the resulting mixture was maintained under agitation for 2 additional hours. Purification was performed by dialyzing the suspension against NaCl 1M (2×) and bidistilled water (5×) before ultrafiltration on MicroSep 100 kDa (Pall, VWR France). Aliquots of 500 µL of USPIO-FUCO ([Fe]=0.05 M) were prepared in 0.15 NaCl and stored at −80° C. until they were used. Average diameters and zeta potentials of USPIO-FUCO and USPIO-CMD were determined using a Zetasizer nano ZS instrument (Malvern Instruments, Orsay, France) and found to be 39.4 nm, −9.0 mV and 65.6 nm, −12.3 mV, respectively.

Relaxation Measurements.

For USPIO-CMD and USPIO-FUCO, relaxivity measurements were performed at different concentrations of compounds in pure water at 37° C. using relaxometers at 20 MHz (0.47 T, Minispec PC-120, Bruker, Karlsruhe, Germany) and at 60 MHz (1.42 T, Minispec mq-60, Bruker, Karlsruhe, Germany).

Blood Clearance Assessment.

In order to determine the biodistribution of USPIO-FUCO in vivo, blood clearance of USPIO-FUCO was assessed via radioactive counting of iterative blood samples. USPIO-FUCO was radiolabeled according to a classical reducing reaction with pertechnetate (Rouzet et al., J. Nucl. Med., 2011, 52: 1433-1440). Sodium pertechnetate ($^{99}TcO_4^-$, about 740 MBq in <100 µL saline, freshly eluted) and 4 µg of stannous chloride (1 µg/µL; Sigma-Aldrich) were added to a vial containing 300 µL of the USPIO-FUCO solution (corresponding to 500 µg of LMW fucoidan), and left to incubate for 1 hour at room temperature. Quality control was performed with instant thin-layer chromatography developed in methyl ethyl ketone buffer. The radiochemical purity was always superior to 99%. For blood clearance assessment, four male Wistar rats were anesthetized with urethan (1.22 g/kg) and a catheter (0.7 mm diameter, Jelco Critikon) was inserted into the left carotid for sampling. Each animal received a single intravenous injection (penis vein) of 20 MBq of $^{99m}$Tc-USPIO-FUCO in a 250 µL volume. Blood samples (250 µL) were taken 5, 15, 30, 45, 60, 90, 120, 180 and 240 minutes post-injection. Saline (250 µL) was injected immediately after each sampling to maintain blood volume and to rinse the catheter. For each sample, one aliquot of 100 µL was taken for well counting (Cobra II, Packard, USA).

Experimental Rat Model.

Male Wistar rats (n=28) were purchased from CEJ (Le Genest, France). Twenty-four (24) rats were involved in the elastase-perfused group, and 4 rats were shame-operated for biodistribution determination. The abdominal aortas of the rats (at 7 weeks of age) were perfused with elastase according to a method previously described (Anidjar et al., Circulation, 1990, 82: 973-981). Briefly, under peritoneal pentobarbital anesthesia (4 mg/100 g body weight; Ceva Santé Animale), about 15 mm of the infrarenal aorta (beginning 2 mm below the left renal artery) was separated from the vena cava. Collateral arteries were exposed from surrounding connective tissue, and were ligated at two places and cut between them. Abdominal aorta was clamped, and a small hole was made to insert a catheter. Micro-catheter was inserted directly below the cephalad side clamping, and then washed with physiologic saline. A distal thread was tightened around the catheter producing a closed perfusion chamber. Four units of pancreatic porcine elastase (E-1250, Sigma) in 550 µL NaCl 9‰ were perfused transmurally for 1 hour, using an automatic pressure perfusion pump. The segment was then rinsed well; flow was re-established, and surgical wounds were closed (Coutard et al., J. Vasc. Res., 2009, 47: 355-366). To localize the treated segment following MRI sessions, at the end of the elastase perfusion, the distance between the upper and lower points of the perfused segment and the left renal artery diameter was measured using a scale within the microscope eyepiece. This model is characterized by the constant presence of a more or less important ILT 2 weeks after induction (Coutard et al., J. Vasc. Res., 2009, 47: 355-366).

The procedure and animal care complied with the "Principles of animal care" formulated by the European Union (Animal Facility Agreement No. 75-18-03, 2005), and animal experimentation was performed under authorization No. 75-101 of the French Ministry of Agriculture.

In vivo MRI.

In vivo MRI experiments were conducted using a 4.7 horizontal bore magnet (Bruket BioSpin47/40, Germany) with 20 cm-wide actively shielded gradient coils (100 mT/m). Six days after operation, the rats were anesthetized with pentobarbital and a right jugular venous catheter was inserted to inject the contrast agent. The animals were divided into 2 groups: Group 1: injection of USPIO-FUCO; Group 2: injection of USPIO-CMD.

The animals were maintained anesthetized using a 1.5% isoflurane/$O_2$ gas mixture (100 cc/min maintenance dose) delivered through a nose cone and placed in a 30 mm birdcage coil with an animal handling system. To confirm correct animal position and localize aortic aneurysm, each animal was scanned using a phase contrast magnetic resonance angiography (MRA) (parameters: TR/TE=17/5.8 msec; flip angle=20°; ETL=1; slice thickness=10 mm; matrix=256×256; FOV=715×331 mm). Axial slices were then acquired along the aorta aneurysm before and after (i.e., 2, 15, 30, 45 and 60 minutes after) injection of 200 µmol of iron/kg of contrast material using a FSPGR T2*-weighted sequence (fast spoiled gradient echo) (parameters/TR/TE=545.6/6.6 msec; flip angle=60°; ETL=1; slice thickness=1 mm; matrix=384×384; FOV=720×330 mm).

Ex vivo MRI.

Two rats with abdominal aneurysm confirmed with FSPGR scan were used. Under deep anesthesia, left common carotid artery was exposed and secured. A small catheter was retrogradely introduced from the middle of the left common carotid artery into the aorta. The abdominal aortic aneurysm was dissected free from surrounding inflammatory adhesions. Using automatic infusion pump, 40 mL of physiologic saline (10 mL/min) were infused using the carotid catheter and washed by cutting the vena cava, followed by infusion of 40 mL of paraformaldehyde (10 mL/min). After sacrifice, the removed aorta was soaked in a tube with paraformaldehyde for ex vivo imaging.

To confirm the precise distribution of USPIO-FUCO, ex vivo high resolution MRI was performed using a Bruker 7T PharmaScan 70/16 equipped with a Bruker 98/38 RF Coil, operated using a Paravision software platform (Bruker, Karlsruhe, Germany). A T2*-mapping sequence with the following parameters was used: echo time=3.8, 9.2 and 14.5 ms; repetition time=852.4 ms; flip angle=30 degree; number of average=1; imaging slice thickness=0.125 mm; image matrix=256×256; field of view=20.141×20 mm; scan time=17 hours and 30 minutes.

Histology.

After in vivo MR imaging, the length and the maximum diameter ($D_{post}$) of the elastase perfused aortic segment were measured using a calibrated grid placed in the dissecting microscope eyepiece. The degree of aortic dilatation (ΔD %) due to elastase infusion was assessed using the following equation:

$$\Delta D(\%) = (D_{post} - D_{pre})/D_{pre} \times 100$$

where $D_{post}$ is the maximum diameter of the aorta before elastase infusion (this diameter was measured during the first surgery). Rats were then euthanized by intravenous pentobarbital overdose. The portion of aorta with dilatation was removed and flushed with saline. In each rat, the aorta was cut into 4 equal tissue rings as follows: one cut was performed in the center of the tissue sample, another cut, in the center of each of the two halves. Four 2 mm rings were thus obtained. One upper ring and one lower ring were fixed in 10% paraformaldehyde for 24 hours and the other two rings were frozen at −20° C. The samples fixed in paraformaldehyde were embedded in paraffin, and cut in 5 mm sections for morphological analysis (Masson trichrome) and immunostaining of P-selectin after antigen retrieval (2 min. ultrasound). A goat anti-mouse P-selectin antibody (SC 6943, Santa Cruz 10 Biotechnology, Santa Cruz, USA) (1/50) was used and was revealed using an anti-goat antibody conjugated to horseradish peroxidise (HRP), followed by a reaction in the presence of 3,3-diaminobenzidine (DAB).

The thickness of thrombi in samples stained with trichrome masson stain was measured by one independent operator using a calibrated grid placed in the optical microscope eyepiece (under a magnification of ×40).

Electron Microscopy.

The tissue samples were first washed with Phosphate Buffer Saline solution (PBS), and then fixed with a mixture of 2% Paraformaldehyde (PFA) and 0.3% glutaraldehyde in 0.1M Phosphate Buffer (PB) (pH 7.4) for 2 hours. Then, small pieces of tissue were post-fixed in 1% PFA in 0.1 PB for prolonged time. The samples were rinsed several times in the same buffer, and then post-fixed with 1% osmium tetroxide for 2 hours. The samples were further rinsed, then progressively dehydrated using graded ethanol, and finally embedded in Epon 812 resin. Ultra-thin sections were taken, placed on carbon coated copper grids, stained with uranyl acetate and lead citrate, and then examined with a JEOL 2010 high-resolution analytical transmission microscope (HRTEM) operated at 200 keV. A Gatan Imaging Filter 2000 system connected to the TEM was offered access to element maps, using energy filtered transmission electron microscope (EFTEM). Chemical composition was established using electron energy-loss spectroscopy (EELS).

Quantification of Signal Enhancement on MR Images.

All image analysis was performed using software (OsiriX DICOM reader v3.7, OsiriX Foundation, Geneva, Switzerland). Maximal artifactual luminal magnetic susceptibility artifact into the aortic lumen, was quantified by the percentage reduction (ΔR %) in aortic luminal area according to a method previously published by the present Applicants (Hyafil et al., Arterioscler. Thromb. Vasc. Biol., 2006, 26: 176-181).

Analysis of arterial wall contrast agent uptake was performed on the 3 slices that anatomically corresponded to sections obtained on histology. On these slices, intra-luminal areas that showed visual intra-luminal signal drop (ILSD) 1 hour after injection of the contrast agent were manually contoured for quantitative signal analysis. These regions of interest (ROI) were pasted on all corresponding images acquired after injection of the contrast agent.

The signal-to-noise ratio (SNR) of aortic wall thrombus was measured by calculating the average signal intensity (SI) in the ROI from MR images at each imaging point ($SNR = [SI_{aortic\ wall} - SI_{muscle}]/SD_{noise\ signal}$). Then, normalized signal enhancement (ΔNSE) was calculated using the following equation:

$$\Delta NSE(\%) = (SNR_{t=n} - SNR_{t=before})/SNR_{t=before} \times 100$$

where 'n' corresponds to the time (in minutes) that separates contrast agent injection and image acquisition (n=2, 15, 30, 45, 60). ΔNSE (%) values for each value of 'n' were plotted, and statistical analyses were performed (Botnar et al., Circulation, 2004, 110: 1463-1466).

Statistical Analysis.

All the statistical analyses were performed using a computer software (Dr.SPSS II for Windows, SPSS Japan Inc. Tokyo). A 1-way ANOVA was carried out to compare the area changes on MRI images between the different groups. Continuous variables were expressed as median and range, and compared using a non-parametric Mann-Whitney U test. An ANOVA test with repeated measures was used to evaluate the time-course of USPIO-FUCO. P<0.05 was considered as indicative of a significant difference between groups.

Results

Relaxivity of the Contrast Agents.

The relaxivity of USPIO-CMD and of USPIO-FUCO (r1 and r2) was determined in water at 37° C. at 20 MHz and 60 MHz. The results obtained are presented in Table 1.

TABLE 1

Relaxivity measurements recorded at 37° C. in water at 20 MHz (0.47T) and 60 MHz (1.42T).

| Contrast agent | Frequency (MHz) | $r_1$ (mM$^{-1}$s$^{-1}$) | $r_2$ (mM$^{-1}$s$^{-1}$) |
|---|---|---|---|
| USPIO-CMD | 20 | 38.8 ± 1.9 | 123 ± 6.2 |
|  | 60 | 15.5 ± 0.7 | 119 ± 5.9 |
| USPIO-FUCO | 20 | 37.5 ± 1.8 | 137 ± 6.9 |
|  | 60 | 15.2 ± 0.7 | 137.4 ± 6.9 |

Blood Clearance of $^{99m}$Tc-USPIO-FUCO in Normal Rats.

Figure 8:
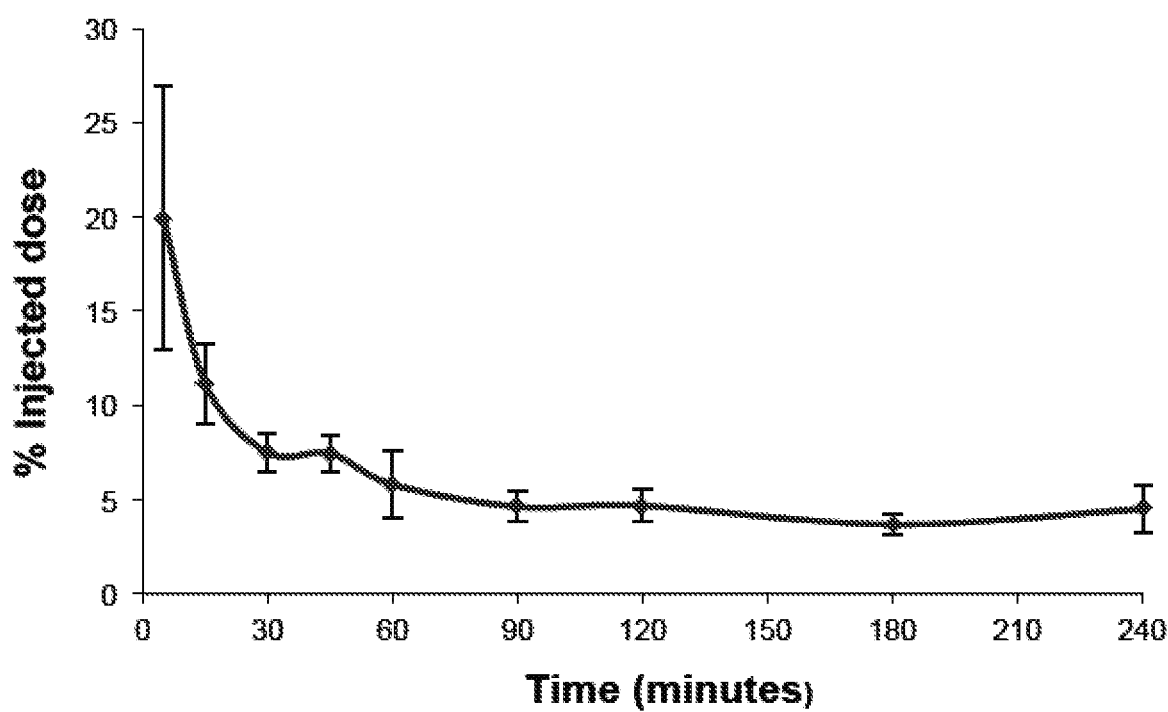
FIG. 8 shows the blood clearance of $^{99}$Tc-USPIO-FUCO (n=4) in normal rats. After correction for residual activity in the injection site and radioactive decay, the results were expressed as the percentage of administered dose remaining in the blood pool as a function of time, assuming that the blood represents 6% of the body weight.

After intravenous injection, $^{99m}$Tc-USPIO-FUCO underwent clearance from the blood according to a 2-compartment model. The rapid component (c) accounted for 70% of the injected activity and had an effective half-life of 9 minutes. The slow component (β) accounted for 30% of the injected activity and had a much longer effective half-life of 316 minutes. Thus, after a rapid decrease following injection, blood activity reached a plateau after 60 minutes at a mean value of 4.4% of the injected dose [3.1%-5.5%](FIG. 8).

Anatomical Characteristics of Aneurysms and Wall Thrombus.

Four rats (3 of which belonged to Group 1 and one of which belonged to Group 2) died before MR imaging. The causes of death included (1) rupture of abdominal aorta (n=2); (2) hindlimb paresis (n=1), and (3) unknown (n=1).

Among the 20 rats that finished MRI examination, all rats (20/20, 100%) showed dilatation of the injured abdominal aorta (average diameter and standard deviation of rat's aortas: proximal diameter, 1.85±0.2 mm: distal diameter, 1.52±0.5 mm: maximal diameter of aneurysmal portion, 5.20±2.1 mm: length of aneurysmal portion, 19.2±2.7 mm: degree of aneurysmal dilatation (ΔD %), 319.2±134.9%). No significant differences between Group 1 and Group 2 were observed in terms of ΔD % and aortic diameter, there was no significant difference between Group 1 and Group 2 (p=0.761 and p=0.490 respectively).

MRI Intraluminal Signal Drop and Thrombus Identification.

Figure 9:
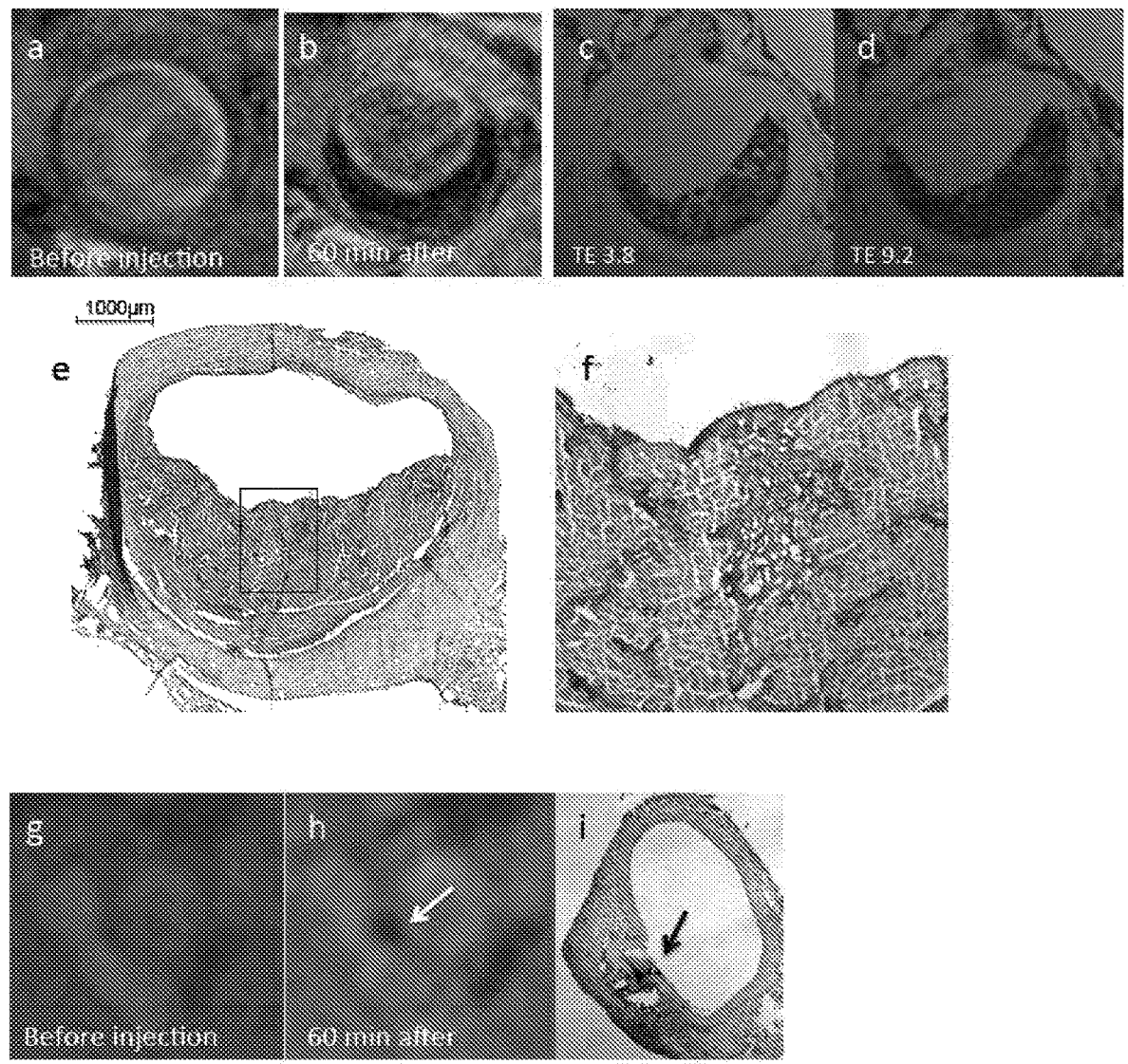
FIG. 9 shows a comparison between the radiological and pathological findings at two different levels. In vivo MRI manifestation (a) before and (b) 60 minutes after venous injection of USPIO-FUCO on large intraluminal thrombus. Ex vivo high resolution T2* weighted images were scanned using two different echo times: (c) TE=3.8 and (d) TE=9.2. Sixty minutes after injection, in vivo MRI showed enhancement on the surface of intraluminal thrombus (b). Expression of P-selectin appeared as a region along the surface of thrombus including grooves of thrombi (e), and magnified view of anti P-selectin stain (f) and short TE T2* weighted images showed more similar distribution than that with longer TE T2* weighted images on ex vivo. T2*WI before (g) and 60 minutes after (h) injection of USPIO-Fuco in the other rat. A small P-selectin positive thrombus (i, arrow) localized at the origin of a ligatured collateral artery corresponds to the region that showed signal enhancement 60 minutes after injection of USPIO-FUCO (h).

In Group 1, all the rats showing thrombus by histology showed a corresponding visual intra-luminal signal drop (ILSD) 1 hour after injection of USPIO-FUCO (FIGS. 9, a and b) and there was no signal drop on healthy parts of the abdominal aorta. In histology, the aortic wall corresponding to the MRI signal drop was always occupied by an ILT with a more or less circular extension along the aortic wall (FIG. 9e). Histologically, there were meshes of P-selectin immunostained foci in the ILT predominantly associated with fibrin and leukocytes, rather than with foci where red blood cell predominated (hemagglutination) (FIG. 9f).

Figure 10:
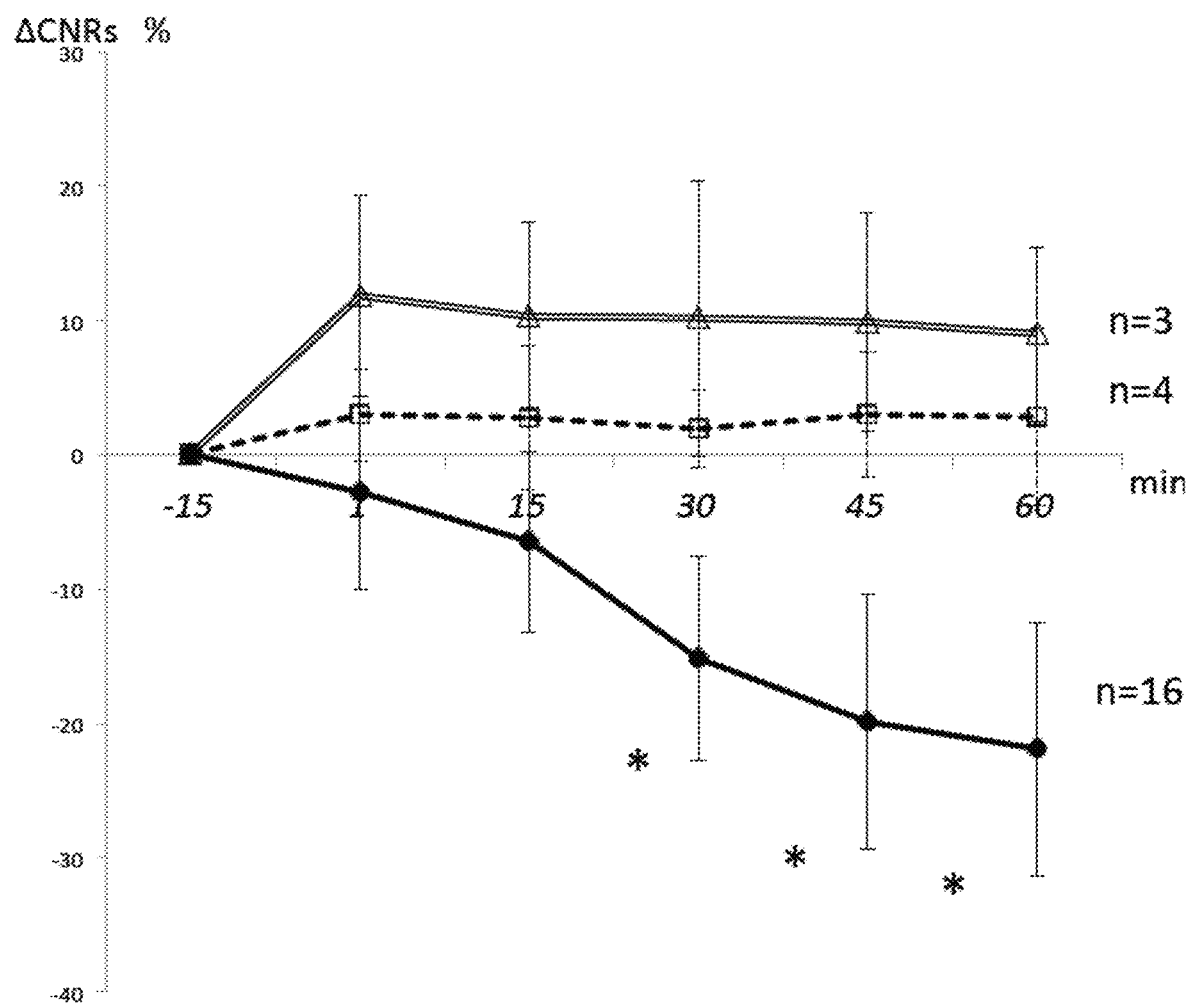
FIG. 10 shows an overtime course of ΔSNE (%) for three different contrast agents injected in the model rats: the MRI agent Sinerem from Guerbert S.A. (triangles), which are USPIO coated with neutral dextran; iron oxide particles coated with dextran (squares); and USPIO-FUCO (circles). Overtime course of ΔSNE (%) for USPIO-FUCO at the site of thrombus pathologically confirmed the correspondence. Pre-contrast MRI was scanned 15 minutes before injection.

An overtime course of the ΔNSE (%) for Group 1 is presented on FIG. 10. In the thrombus areas, ILSD could be detected as early as 15 minutes after injection of USPIO-FUCO and was maximum 1 hour after injection (15 min, p<0.05; 30 min, 45 min, 60 min, p<0.001). Thrombus thickness measured on MR images 1 hour after USPIO-FUCO injection showed an excellent correlation with histology at the corresponding level ($r^2$=0.90) although MRI consistently overestimated thrombus thickness compared to histology. The minimal thickness of thrombus that could be detected by MRI (FIG. 9h) was 130 μm on histological section (FIG. 9i). No visual ILSD could be identified in rats from Group 2.

When comparing Group 1 and Group 2 in terms of luminal area before and 1 hour after injection of the contrast agent, in the areas of thrombus identified by histology, rats injected with USPIO-FUCO showed a larger area reduction (ΔR %) than rats injected with USPIO-CMD (p<0.001) (FIG. 12).

Ex vivo MRI.

On images acquired with a short echo time (3.8 ms), a heterogeneous signal with meshes of signal drop similar was observed in the thrombus areas similar to what was observed on P-selectin-immunostained slices. This heterogeneity was not visible at higher TE. On T2* maps, a large heterogeneity was observed.

Electron Microscopy.

Confirmation of the presence of iron nanoparticles in the thrombus was obtained using electron microscopy (FIG. 13). Iron nanoparticles were observed as a hyperdense signal, predominantly in fibrin rich areas of the thrombus.

Discussion

The present example shows that, through P-selectin molecular imaging: USPIO-FUCO (1) allowed visualization of platelet-rich thrombus with high sensitivity in a rat model, (2) within 30 minutes after injection, and (3) with an excellent selectivity at a tissue level of adhesion and retention of the nanoparticles.

Relaxivity of the Contrast Agents.

The relaxivities r1 and r2 were found to be identical for both contrast agents at a given frequency. The increase in r2 from USPIO-CMD to USPIO-FUCO is in accordance with the increase in size of the nanoparticles from 39.4 nm to 65.6 nm, respectively (Geraldes et al., Contrast Media Mol. Imaging, 2009, 4: 1-23).

P-Selectin Targeted Imaging Agents.

As demonstrated herein, USPIO-FUCO shows a high specificity for P-selectin. USPIOs are mostly used as MRI contrast agents due to their negative enhancement effect on T2- and T2*-weighted sequences. However, in addition to the T2 and T2* effects, USPIOs also exhibit a T1 effect (Chambon et al., Magn. Reson. Imaging, 1993, 11: 509-519; Canet et al., Magn. Reson. Imaging, 1993, 11: 1139-1145). In the present study, there was no detectable T1 effect on the aortic wall using either USPIO-FUCO or USPIO-CMD. The T2* effect using USPIO-FUCO was however highly visible with a strong ILSD 1 hour after injection in the area corresponding to the thrombus on histology. This strong ILSD was not visible after injection of USPIO-CMD, suggesting that USPIO-CMD might act like non-specific USPIOs which are phagocytized 24-48 hours after injection (Hyafil et al., Arterioscler. Thromb. Vasc. Biol., 2006, 26: 176-181; Ruehm et al., Circulation, 2001, 103: 415-422).

Distribution of P-Selectin.

Enlargement of abdominal aortic aneurysm involves proteolytic degradation of media, adventitial inflammation and fibrosis, and the formation of an intraluminal thrombus. It has also been suggested that the biological activity of ILT could be one of the driving forces in aneurismal evolution (Michel et al., Cardiovasc. Res., 2011, 90: 18-27).

Interestingly, in the present MRI experiments, a high variability of USPIO-FUCO uptake within the thrombus was observed, with a heterogeneous signal and T2* showing meshes of low signal and short T2* areas. This distribution looked very similar to that observed by histology after P-selectin immunostaining, suggesting the presence of higher concentrations of USPIO-FUCO in areas rich in P-selectin-rich fibrin than in RBC-rich areas. Unfortunately, due to the large difference in slice thickness between MRI and histology (125 μm and 5 μm, respectively), it was not possible to conclude definitely regarding this point.

Utility.

Though it has been considered that targeted iron oxide microparticles detected by MRI requires an imaging duration of several hours, in the present study, it took less than 30 minutes to depict an intravascular thrombus with high sensitivity. Since MRI is now the gold standard (Takaya et al., Circulation, 2005, 111: 2768-2775) for detecting intraplaque hemorrhages in at risk atherothrombotic patients (Michel et al., Eur. Heart J., 2011, 32: 1977-1985), the use of USPIO-FUCO, which can detect P-selectin with high sensitivity, will be a powerful adjuvant for sensitizing MRI in the detection of vulnerable plaque.

Perl blue stain is an established method allowing detection of iron in biological tissues. However, it cannot distinguish the origin (i.e., endogenous or exogenous) of iron particles. In the present study, endogenous iron may result from the operational procedure used for causing aneurysm and thrombus, and was confirmed on T2* weighted images before injection of the contrast agent. In the USPIO-FUCO nanoparticles, the fucoidan constitutes the outer-shell of the particles. In a preliminary experiment, USPIO inside USPIO-FUCO nanoparticles could not detected using conventional Perl-Blue staining. This might be due to a large number of electron charges around the fucoidan. Consequently, electron microscopy was used to confirm the ILT location of USPIO.

The fact that gradient echo MR sequences are more sensitive than spin-echo sequences for detecting the contrast agent, results from the inherent T2* sensitivity of these sequences (Foster-Gareau et al., Magn. Reson. Med., 2003, 49: 968-971). Signal attenuation from USPIOs due to their T2*/T2 effect can produce artifacts distorting the assessment of the size of the contrasted area (Corot et al., Adv. Drug Deliv. Rev., 2006, 58: 1471-1504). The degree of magnetic susceptibility effect (blooming effect) can be controlled by specifying data acquisition parameters that have more or less T2 and T2* dependence. The extent of signal attenuation is not directly proportional to the concentration of iron nanoparticles, because the blooming effect may extend to some distance depending on the imaging parameters. Therefore, it could make the actual size larger than the lesion. The present data confirm this potential overestimation by showing, despite an excellent correlation between MRI and histology for thrombus thickness measurement ($r^2$=0.90) (FIG. 11B), a consistently thicker ILT by MRI (p<0.0001). Fortunately, thanks to this overestimation, it is possible to detect very small thrombi attached to the aortic wall with sizes as small as 100 μm (FIG. 9 g-i). This might be very useful to detect culprit atherosclerotic plaques, in particular in stroke patients.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for monitoring the response of a patient suffering from a clinical condition associated with selectins to a treatment for said clinical condition, the method comprising steps of:

contacting a biological system obtained from said patient with an effective amount of a selectin-targeted imaging agent or administering to the patient an effective amount of a selectin-targeted imaging agent, wherein said patient has received the treatment for said clinical condition, and detecting any selectin bound to the imaging agent using an imaging technique, wherein detection of selectin bound to the imaging agent is indicative of the response of the patient to said treatment, wherein the selectin-targeted imaging agent comprises at least one fucoidan moiety directly complexed to technetium-99m ($^{99m}$Tc), and the at least one fucoidan moiety has an average molecular weight of about 2000 to about 8000 Da, and wherein the clinical condition associated with selectins is myocardial ischemia/reperfusion injury.

2. The method according to claim 1, wherein the at least one fucoidan moiety binds to at least one human selectin selected from the group consisting of P-selectin, L-selectin and E-selectin, with a dissociation constant of between about 0.1 nM and about 500 nM.

3. The method according to claim 1, wherein said method comprises the step of contacting the biological system from said patient with an effective amount of a selectin-targeted imaging agent, and the biological system is selected from the group consisting of a cell, a biological fluid and a biological tissue.

4. The method according to claim 1, wherein the step of detecting any selectin bound to the imaging agent using an imaging technique comprises:

comparing an image obtained in the detecting step by imaging the biological system or part of the patient's body with an image obtained under the same conditions before the patient has received the treatment for the clinical condition associated with selectins, wherein comparing the images allows the response of the patient to said treatment to be monitored.

* * * * *